US010725040B2

(12) United States Patent
Das et al.

(10) Patent No.: US 10,725,040 B2
(45) Date of Patent: *Jul. 28, 2020

(54) PROTEOMICS BASED DIAGNOSTIC DETECTION METHOD FOR CHRONIC SINUSITIS

(71) Applicants: NATIONWIDE CHILDREN'S HOSPITAL, INC., Columbus, OH (US); THE OHIO STATE UNIVERSITY, Columbus, OH (US)

(72) Inventors: Subinoy Das, Columbus, OH (US); Lauren O. Bakaletz, Hilliard, OH (US)

(73) Assignees: NATIONWIDE CHILDREN'S HOSPITAL, INC., Columbus, OH (US); THE OHIO STATE UNIVERSITY, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/450,476

(22) Filed: Jun. 24, 2019

(65) Prior Publication Data

US 2019/0324037 A1 Oct. 24, 2019

Related U.S. Application Data

(60) Continuation of application No. 16/039,031, filed on Jul. 18, 2018, now Pat. No. 10,345,300, which is a continuation of application No. 15/404,681, filed on Jan. 12, 2017, now Pat. No. 10,048,261, which is a division of application No. 14/124,470, filed as application No. PCT/US2012/040910 on Jun. 5, 2012, now Pat. No. 9,568,472.

(60) Provisional application No. 61/493,829, filed on Jun. 6, 2011.

(51) Int. Cl.

| G01N 33/53 | (2006.01) |
| A61K 39/00 | (2006.01) |
| A61K 39/07 | (2006.01) |
| G01N 33/569 | (2006.01) |
| C12Q 1/04 | (2006.01) |
| A61B 10/00 | (2006.01) |

(52) U.S. Cl.
CPC .... G01N 33/56911 (2013.01); A61B 10/0045 (2013.01); C12Q 1/04 (2013.01); *G01N 2333/285* (2013.01); *G01N 2800/12* (2013.01); *G01N 2800/14* (2013.01)

(58) Field of Classification Search
CPC .................. A61K 39/00; A61K 39/07
USPC .......... 424/130.1, 164.1, 184.1, 234.1, 256.1
See application file for complete search history.

(56) References Cited

U.S. PATENT DOCUMENTS

| 5,415,994 A | 5/1995 | Imrich et al. |
| 5,656,448 A | 8/1997 | Kang et al. |
| 5,763,262 A | 6/1998 | Wong et al. |
| 9,568,472 B2 * | 2/2017 | Das .......................... C12Q 1/04 |
| 10,048,261 B2 * | 8/2018 | Das .......................... C12Q 1/04 |
| 10,345,300 B2 * | 7/2019 | Das .................... A61B 10/0045 |
| 2002/0164354 A1 | 11/2002 | Barenkamp |
| 2008/0254997 A1 | 10/2008 | Oku et al. |
| 2012/0276145 A1 | 11/2012 | Webster et al. |

FOREIGN PATENT DOCUMENTS

| JP | S62148859 A | 7/1987 |
| WO | WO-2010/092176 A2 | 8/2010 |

OTHER PUBLICATIONS

Bakaletz et al., Frequency of fimbriation of nontypable Haemophilus influenzae and its ability to adhere to chinchilla and human respiratory epithelium, *Infection and Immunity*, 56(2):331-5 (1988).

Butler, Solid supports in enzyme-linked immunosorbent assay and other solid-phase immunoassays, *Methods*, 22:4-23 (2000).

Duim et al., Molecular variation in the major outer membrane protein P5 gene of nonencapsulated Haemophilus influenzae during chronic infections, *Infect. Immun.*, 65(4):1351-6 (1997).

Esmaily et al., Efficacy of immunization with outer membrane proteins for induction of pulmonary clearance of nontypeable Haemophilus influenzae in a rat respiratory model, *Iran J. Allergy, Asthma Immunol.*, 5(2):57-61 (2006).

Gallaher et al., Identification of biofilm proteins in non-typeable Haemophilus Influenzae, *BMC Microbiol.*, 6(1):65 (2006).

International Search Report and Written Opinion of the International Searching Authority, European Patent Office, PCT/US2010/040910, dated Oct. 22, 2012.

Ishida et al., Effects of macrolides on antigen presentation and cytokine production by dendritic cells and T lymphocytes, *Int. J. Pediatr. Otorhinolaryngol.*, 71(2):297-305 (2007).

(Continued)

*Primary Examiner* — Rodney P Swartz
(74) *Attorney, Agent, or Firm* — Marshall, Gerstein & Borun LLP

(57) ABSTRACT

The invention provides for a proteomic approach for identification of specific bacterial protein profiles that may be used in the development of methods for the diagnosis of bacterial chronic sinusitis. The invention provides for methods for determining the presence of pathogenic bacteria in the upper respiratory tract of a subject using protein profiles of the pathogenic bacteria. The invention also provides for methods of diagnosing a bacterial infection of the upper respiratory tract of a subject using protein profiles of a pathogenic bacteria. In addition, the invention provides for devices, immunoassays and kits for identifying pathogenic bacteria in the upper respiratory tract.

19 Claims, 3 Drawing Sheets

Specification includes a Sequence Listing.

(56) References Cited

OTHER PUBLICATIONS

Krasan et al., Adhesin expression in matched nasopharyngeal and middle ear isolates of nontypeable Haemophilus influenzae from children with acute otitis media, *Infect. Immun.*, 67(1):449-54 (1999).

Novotny et al., Transcutaneous immunization as preventative and therapeutic regimens to protect against experimental otitis media due to nontypeable Haemophilus influenzae, *Mucosal Immunol.*, 4(4):456-67 (2011).

Ogino, Bacteriological Findings in Chronic Sinusitis, English abstract, *Otolaryngology*, 55(5):347-53 (1983).

Oliveira et al., Computer-based analysis of Haemophilus parauis protein fingerprints, *Canadian J. Vet. Res.*, 68(1):71-5 (2004).

Perkins et al., Probability-based protein identification by searching sequence databases using mass spectrometry data, *Electrophoresis*, 20(18):3551-67 (1999).

Qu et al., Proteomic expression profiling of Haemophilus influenzae grown in pooled human sputum from adults with chronic obstructive pulmonary disease revealantioxidant and stress responses, *BMC Microbiol.*, 10(1):162 (2010).

Villasenor-Sierra et al., Memebrane protein profile of paired nasopharyngeal and middle ear isolate of nontypable Haemophilus influenzae from Mexican children with acute otitis media, *Clin. Infect. Dis.*, 28(2):268 (1999).

* cited by examiner

PROTEOMICS BASED DIAGNOSTIC DETECTION METHOD FOR CHRONIC SINUSITIS

This application is a Continuation of U.S. Ser. No. 16/039,031 (now U.S. Pat. No. 10,345,300), filed Jul. 18, 2018, which is a Continuation of U.S. Ser. No. 15/404,681, filed Jan. 12, 2017 (now U.S. Pat. No. 10,048,261), which is a Divisional of U.S. patent application Ser. No. 14/124,470, filed Jun. 16, 2014 (now U.S. Pat. No. 9,568,472), which is the U.S. National Phase of International Application No. PCT/US2012/040910, filed Jun. 5, 2012, which claims priority benefit of U.S. Provisional Patent Application No. 61/493,829, filed Jun. 6, 2011, which are incorporated by reference herein in their entirety.

This invention was made with government support under Grant Nos. R01 DC05847 and KL2RR025754 awarded by the United States National Institutes of Health. The United States government has certain rights in the invention.

FIELD OF INVENTION

The invention provides for a proteomic approach for identification of specific bacterial protein profiles that may be used in the development of methods for the diagnosis of bacterial chronic sinusitis. The invention provides for methods of determining the presence for pathogenic bacteria in the upper respiratory tract of a subject using protein profiles of the pathogenic bacteria. The invention also provides for methods of diagnosing a bacterial infection of the upper respiratory tract of a subject using protein profiles of the pathogenic bacteria. In addition, the invention provides for devices, immunoassays and kits for identifying pathogenic bacteria in the upper respiratory tract.

BACKGROUND

Otitis media, sinusitis, bronchitis, pharyngitis, and non-specific upper respiratory tract infections (URTI) account for approximately 75% of outpatient antibiotic prescriptions in the United States. Antibiotic use remains high despite the fact that greater than 85% of these infections are due to viruses and resolve without complication. Nonetheless, those remaining infections that are indeed due to bacterial pathogens require more effective management than is currently available. Bacterial cultures provide limited diagnostic value because the most common bacteria responsible for URTI are also often commensal organisms in the nasopharynx.

Infections of the upper airway are the number one reason for office visits in the US (American Academy of Pediatrics. *Pediatrics*, 2004. 113:1451-1456. Center for Disease Control and Prevention web site, Gonzales R, et al. *JAMA*, 1997. 278(11):901-904, Nyquist A-C. *JAMA*, 1998. 279(11): 875-877). About 52% of adults patients and 45% of pediatric patients are prescribed antibiotics when diagnosed with an upper airway infection (Gonzales R, et al. *JAMA*, 1997. 278(11):901-904, Nyquist A-C. *JAMA*, 1998. 279(11): 875-877). Upper airway infections are multifactorial and polymicrobial diseases. Infection by respiratory viruses (e.g. RSV, adenovirus, rhinovirus, parainfluenza virus) predisposes to bacterial superinfection by members of the nasopharynx normal flora: nontypeable *Haemophilus influenzae*, *Streptococcus pneumoniae* and *Moraxella catarrhalis*. While viral infections are often self-limiting, therapeutic delay of bacterial disease can lead to complications, permanent sequalae and severe morbidity and mortality.

Diagnosis is mainly based on clinical manifestations. Signs and symptoms of disease of bacterial and nonbacterial etiologies are often indistinguishable. Specific bacterial identification by traditional microbiological culture techniques often fail to detect microorganisms growing within biofilms. Contamination of specimens by resident colonizing flora often results in laboratory culture reports of uncertain clinical value. Indiscriminate antibiotic use modifies the commensal flora in the nasopharynx and induces the selection and emergence of microorganisms resistant to common antibiotics. Despite a decreasing trend in antibiotic prescription in recent years, unnecessary and inappropriate antibiotic therapies are common, particularly in the treatment of otitis media and sinusitis.

Upper respiratory tract infection remains as a major cause of overuse of antibiotics and, therefore, a major contributor to the widespread emergence of antibiotic resistance. Therefore, there is a need for early and rapid diagnostic tests that could discriminate between commensal and pathogenic bacteria. These tests would promote judicious use of antibiotic therapy, promote more effective choice of treatment and improve outcomes.

SUMMARY OF INVENTION

Due to unique growth characteristics, bacterial biofilms produce a distinct set of proteins may be used to distinguish between commensal and pathogenic states. The invention provides for methods of identifying the protein profile of bacterial biofilms. The methodology involves detecting trace quantities of signature proteins that identify specific bacterial pathogens from typically sterile sites in the paranasal sinus cavities. As described herein, biofilms produced by nontypeable *Haemophilus influenzae* (NTHI) over 10 days generate a specific protein profile. Biofilms formed by NTHI in vitro release a signature set of proteins into their environment that remains identifiable for several days. Outer membrane proteins (OMPs) are predominant components of the NTHI biofilm supernatant. Of particular interest are major OMPs associated with bacterial virulence: outer membrane protein P5 (OMP P5) and outer membrane protein P2 (OMP P2). Additional OMPs include high molecular weight adhesin 1/high molecular weight adhesin 2 (HMW1/HMW2), and IgA-protease. HMW1/HMW2, OMP P5 are mediators of adhesion to epithelial cells, OMP P2 is a porin and IgA protease functions to cleave host IgA.

These studies support the development of a clinical diagnostic test and device for early and rapid identification of NTHI-associated URTIs, leading to a more effective choice of treatment and improved outcomes. NTHI was used as an example for the study but the same methods may be used to identify the presence of any pathogenic bacteria including those known to cause chronic sinusitis such as *Haemophiius influenza, Streptococcus pneumoniae, Moraxella catarrhalis, Staphylococcus aureus, Pseudomonas aeruginosa* and *Stenotrophomonas maltophilia*.

The invention also provides for an immunoassay device that involves obtaining a sample of the secretions within the typically sterile paranasal sinus cavities, and rapidly detecting the presence of trace quantities of signature proteins that identify specific bacterial pathogens from these typically sterile sites.

The invention provides for methods of detecting the presence of a pathogenic bacteria in the upper respiratory tract of a subject comprising the steps of: a) obtaining a sample of secretions from the upper respiratory tract of the subject; b) generating a protein profile of the sample; c)

comparing the protein profile with a reference protein profile, wherein the reference protein profile identifies a pathogenic bacteria; and d) determining whether the protein profile of the sample associates to the reference protein profile, wherein association is indicative of the presence of the pathogenic bacteria in the upper respiratory tract of the subject.

The invention also provides for methods of detecting the presence of a pathogenic bacteria in the upper respiratory tract of a subject as described above wherein the method further comprises the step of administering a therapeutic compound to reduce or eliminate the pathogenic bacteria in the upper respiratory tract of the subject. Exemplary therapeutic compounds that reduce or eliminate pathogenic bacteria in the upper respiratory tract include antibiotics such as penicillin, erythromycin, amoxicillin, thimethoprim-sulfamethoxazole, doxycyline, cefpodoxime, cefuroxime, cefdinir, clarithromycin, azithromycin, levofloxacin, gatifloxacin, and moxifloxacin, alpha-adreneric agonists such as oxymetazoline hydrochloride, anticholinergic (parasympatholytic) agents such as ipratropium bromide, antihistamines such as chlorpheniramine maleate, beta-agonist bronchodilators, non-steroidal anti-inflammatory drugs, camphor, menthol, *Echinacea*, mast cell stabilizers such as cromolyn sodium, topical nasal steroids such as fluticasone propionate and zinc salts.

The invention also provides for methods of detecting the presence of a pathogenic bacteria in the upper respiratory tract of a subject as described above wherein the method further comprises the step of informing the subject of the presence or absence of the pathogenic bacteria in the upper respiratory tract.

The invention also provides for methods of detecting the presence of a pathogenic bacteria in the upper respiratory tract of a subject as described above wherein the method further comprises the step of diagnosing the subject with a bacterial infection, wherein the presence of the pathogenic bacteria in the upper respiratory tract of the subject is indicative of a bacterial infection.

The term "pathogenic bacteria" refers to any disease causing bacteria. The term "commensal bacteria" refers to harmless or non-disease causing bacteria. The methods of the invention also may be used to distinguish the presence of commensal bacteria verses pathogenic bacteria in the upper respiratory tract of a subject.

The invention also provides for methods of diagnosing a bacterial infection in the upper respiratory tract of a subject comprising the steps of: a) obtaining a sample of secretions from the upper respiratory tract of the subject; b) generating a protein profile of the sample; c) comparing the protein profile of the sample with a reference protein profile, wherein the reference protein profile identifies a pathogenic bacteria; and d) determining whether the protein profile of the sample associates to the protein profile; wherein association is indicative of a bacterial infection in the upper respiratory tract of the subject.

The invention also provides for methods of diagnosing a bacterial infection in the upper respiratory tract of a subject as described above wherein the method further comprises the step of the step of informing the subject of the diagnosis of a bacterial infection in the upper respiratory tract.

The invention also provides for methods of diagnosing a bacterial infection in the upper respiratory tract of a subject as described above wherein the method further comprises the step of administering a therapeutic compound to treat the bacterial infection. A treatment for a bacterial infection will reduce or alleviate the symptoms caused by the pathogenic bacteria or eliminate the bacteria from the site of infection. Exemplary therapeutic compounds that treat a bacterial infection in the upper respiratory tract include antibiotics such as penicillin, erythromycin, amoxicillin, thimethoprim-sulfamethoxazole, doxycyline, cefpodoxime, cefuroxime, cefdinir, clarithromycin, azithromycin, levofloxacin, gatifloxacin, and moxifloxacin, alpha-adreneric agonists such as oxymetazoline hydrochloride, anticholinergic (parasympatholytic) agents such as ipratropium bromide, antihistamines such as chlorpheniramine maleate, beta-agonist bronchodilators, non-steroidal anti-inflammatory drugs, camphor, menthol, *Echinacea*, mast cell stabilizers such as cromolyn sodium, topical nasal steroids such as fluticasone propionate, budenoside, mometasone, triamcinolone, and dexamethasone, and zinc salts. The term "protein profile" refers to at least one protein that is at least partially identified or characterized so that the presence or absence of the protein in any particular sample may be monitored. The term "reference protein profile" refers to a protein profile generated for a known control or standard sample.

A protein profile of a sample associates with a reference protein profile when one or more the proteins in the reference profile are present in the sample profile at a concentration that indicates infection or pathogenicity of the bacteria. To determine if a sample protein profile associates with a reference protein profile, the profiles are scored to predict how likely the mass of a fragment that it detected is likely from the peptide sequence it is predicted it to be, and how much quantity of the peptide there is in the supernatant. Software programs that analyze mass spectrometry data may be used. For example, Mascot (Matrix Science, Boston, Mass.), performs mass spectrometry data analysis through a statistical evaluation of matches between observed and projected peptide fragments rather than cross correlation may be used to determine in the sample associates with a reference protein profile. See, e.g., D. N. Perkins, et al., Electrophoresis, 20(18) 3551-67 (1999).

The preceding methods may be carried out for any pathogenic bacteria which infects the upper respiratory tract, including *Haemophilus influenzae, Streptococcus pneumoniae, Moraxella catarrhalis, Staphylococcus aureus, Pseudomonas aeruginosa* or *Stenotrophomonas maltophilia*.

The invention also provides for uses of a therapeutic compound for the preparation of a medicament to reduce or eliminate the pathogenic bacteria in the upper respiratory tract of a subject or uses to treat a bacterial infection in the upper respiratory tract of a subject, wherein the subject has a protein profile that associates to a reference protein profile, and wherein the association is indicative of the presence of the pathogenic bacteria or bacterial infection in the upper respiratory tract of the subject as determined by any of the preceding methods of detecting the presence of a pathogenic bacteria or diagnosing a bacterial infection in the upper respiratory tract of a subject.

The invention also provides for therapeutic compositions for the reduction or elimination of a pathogenic bacteria in the upper respiratory tract of a subject or for the treatment of a bacterial infection in the upper respiratory tract of a subject, wherein the subject has a protein profile that associates to a reference protein profile, and wherein the association is indicative of the presence of the pathogenic bacteria or bacterial infection in the upper respiratory tract of the subject tract of the subject as determined by any of the preceding methods of detecting the presence of a pathogenic bacteria or diagnosing a bacterial infection in the upper respiratory tract of a subject.

Exemplary therapeutic compounds that treat a bacterial infection in the upper respiratory tract include antibiotics such as penicillin, erythromycin, amoxicillin, thimethoprim-sulfamethoxazole, doxycyline, cefpodoxime, cefuroxime, cefdinir, clarithromycin, azithromycin, levofloxacin, gatifloxacin, and moxifloxacin, alpha-adreneric agonists such as oxymetazoline hydrochloride, anticholinergic (parasympatholytic) agents such as ipratropium bromide, antihistamines such as chlorpheniramine maleate, beta-agonist bronchodilators, non-steroidal anti-inflammatory drugs, camphor, menthol, *Echinacea*, mast cell stabilizers such as cromolyn sodium, topical nasal steroids such as fluticasone propionate, budenoside, mometasone, triamcinolone, and dexamethasone, and zinc salts.

In another aspect of the invention, the invention provides for methods of detecting the presence of nontypeable *Haemophilus influenzae* (NTHI) bacteria in the upper respiratory tract of a subject comprising the steps of: a) obtaining a sample from the upper respiratory tract of the subject; b) detecting the presence of at least one biomarker in the sample, wherein the biomarkers are selected from the group consisting of: HMW1/HMW2, OMP P5, OMP P2 and IgA-protease, and wherein the presence of at least one biomarker indicates the presence of NTHI bacteria in the upper respiratory tract of the subject. In one embodiment, the method comprises detecting the presence of OMP P2 and/or OMP P5 in the sample, wherein the presence of OMP P2 and/or OMP P5 indicates the presence of NTHI bacteria in the upper respiratory tract of the subject.

The invention also provides for methods of detecting the presence of NTHI bacteria in the upper respiratory tract of a subject wherein the method further comprises the step of administering a therapeutic compound to reduce or eliminate the NTHI bacteria in the upper respiratory tract of the subject. Exemplary therapeutic compounds that reduce or eliminate the NTHI bacteria in the upper respiratory tract include antibiotics such as penicillin, erythromycin, amoxicillin, thimethoprim-sulfamethoxazole, doxycyline, cefpodoxime, cefuroxime, cefdinir, clarithromycin, azithromycin, levofloxacin, gatifloxacin, and moxifloxacin, alpha-adreneric agonists such as oxymetazoline hydrochloride, anticholinergic (parasympatholytic) agents such as ipratropium bromide, antihistamines such as chlorpheniramine maleate, beta-agonist bronchodilators, non-steroidal anti-inflammatory drugs, camphor, menthol, *Echinacea*, mast cell stabilizers such as cromolyn sodium, topical nasal steroids such as fluticasone propionate, budenoside, mometasone, triamcinolone, and dexamethasone, and zinc salts.

The invention also provides for methods of diagnosing a NTHI infection in the upper respiratory tract of a subject comprising the steps of: a) obtaining a sample of secretions from the upper respiratory tract of the subject, b) detecting the presence of at least one biomarker in the sample, wherein the biomarkers are selected from the group consisting of: HMW1/HMW2. OMP P5, OMP P2 and IgA-protease, and wherein the presence of at least one biomarkers indicates an NTHI infection in the upper respiratory tract of the subject. In one embodiment, the method comprises detecting the presence of OMP P2 and/or OMP P5 in the sample, wherein the presence of OMP P2 and/or OMP P5 indicates a NTHI bacterial infection in the upper respiratory tract of the subject.

The invention also provides for methods of diagnosing a NTHI infection in the upper respiratory tract of a subject as described above wherein the method further comprises the step of informing the subject of the diagnosis of a NTHI infection in the upper respiratory tract.

The invention also provides for methods of diagnosing NTHI infection in the upper respiratory tract of a subject as described above wherein the method further comprises the step of administering a therapeutic compound to treat the NTHI infection in the upper respiratory tract of the subject. A treatment for a NTHI infection will reduce or alleviate the symptoms caused by the NTHI bacteria or eliminate the NTHI bacteria from the site of infection. Exemplary therapeutic compounds that treat a NTHI infection in the upper respiratory tract include antibiotics such as penicillin, erythromycin, amoxicillin, thimethoprim-sulfamethoxazole, doxycyline, cefpodoxime, cefuroxime, cefdinir, clarithromycin, azithromycin, levofloxacin, gatifloxacin, and moxifloxacin, alpha-adreneric agonists such as oxymetazoline hydrochloride, anticholinergic (parasympatholytic) agents such as ipratropium bromide, antihistamines such as chlorpheniramine maleate, beta-agonist bronchodilators, non-steroidal anti-inflammatory drugs, camphor, menthol, *Echinacea*, mast cell stabilizers such as cromolyn sodium, topical nasal steroids such as fluticasone propionate, budenoside, mometasone, triamcinolone, and dexamethasone, and zinc salts.

The term "upper respiratory tract" includes the nose or nostrils, nasal cavity, mouth, throat (pharynx), paranasal sinus cavity and voice box (larynx). The respiratory system is lined with a mucous membrane that secretes mucus or fluid. This secreted mucus and fluid is referred to herein as "secretions." In any of the preceding methods, the sample of secretions may be collected from the paranasal sinus cavity including the middle meatus or the ethmoid infundibulum. The "paranasal sinus cavity" refers to the frontal sinuses (in the forehead), maxillary sinuses (behind the cheek bones), ethmoid sinuses (between the eyes) and the sphenoid sinuses (behind the eyes).

The invention also provides for use of a therapeutic compound for the preparation of a medicament to reduce or eliminate NTHI bacteria in the upper respiratory tract of a subject or to treat a NTHi infection in the upper respiratory tract of a subject, wherein the presence of NTHI bacteria or a NTHI infection is determined by the presence of at least one biomarker selected from OMP P2 and OMP P5 as determined by any of the preceding methods of detecting the presence of a NTHI bacterial or diagnosing a NTHI infection in the upper respiratory tract of a subject method as determined by the preceding methods of detecting the presence of NTHI bacteria or diagnosing a NTHI infection in the upper respiratory tract of a subject.

The invention also provides for a therapeutic composition for the reduction or elimination of NTHI bacteria or for the treatment of NTHI infection in the upper respiratory tract of a subject, wherein the presence of NTHi bacteria or NTHI infection as determined by any of the preceding methods of detecting the presence of a NTHI bacterial or diagnosing a NTHI infection in the upper respiratory tract of a subject.

Any of the preceding methods, uses or therapeutic compositions may be carried out on a subject suffering from chronic sinusitis, or a subject that is prone to suffering from recurrent acute sinusitis. In addition, any of the preceding methods may be carried out on a subject suffering from Otitis media, bronchitis, pharyngitis, and nonspecific upper respiratory tract infections.

The invention also provides for methods, uses or therapeutic compositions for treating chronic sinusitis or a pathogenic bacterial infection of the upper respiratory tract in a subject comprising detecting a pathogenic bacteria in the upper respiratory tract of the subject using any of the preceding methods and administering the appropriate dose of a therapeutic compound known to effectively treat the particular pathogenic bacteria detected within the upper respiratory tract of the subject. A treatment for a chronic sinusitis or a pathogenic bacterial infection will reduce or alleviate the symptoms caused by the pathogenic bacteria or eliminate the pathogenic bacteria from the site of the infection. Exemplary therapeutic compounds include antibiotics such as penicillin, erythromycin, amoxicillin, thimethoprim-sulfamethoxazole, doxycyline, cefpodoxime, cefuroxime, cefdinir, clarithromycin, azithromycin, levofloxacin, gatifloxacin, and moxifloxacin, alpha-adreneric agonists such as oxymetazoline hydrochloride, anticholinergic (parasympatholytic) agents such as ipratropium bromide, antihistamines such as chlorpheniramine maleate, beta-agonist bronchodilators, non-steroidal anti-inflammatory drugs, camphor, menthol, *Echinacea*, mast cell stabilizers such as cromolyn sodium, topical nasal steroids such as fluticasone propionate, budenoside, mometasone, triamcinolone, and dexamethasone, and zinc salts.

The invention also provides for methods of treating, uses and therapeutic compositions for chronic sinusitis or a pathogenic bacterial infection of the upper respiratory tract in a subject comprising diagnosing a pathogenic bacteria infection in the upper respiratory tract of the subject using any of the preceding methods and administering the appropriate dose of a therapeutic compound known to effectively treat the particular pathogenic bacteria detected within the upper respiratory tract of the subject. Exemplary therapeutic compounds include antibiotics such as penicillin, erythromycin, amoxicillin, thimethoprim-sulfamethoxazole, doxycyline, cefpodoxime, cefuroxime, cefdinir, clarithromycin, azithromycin, levofloxacin, gatifloxacin, and moxifloxacin, alpha-adreneric agonists such as oxymetazoline hydrochloride, anticholinergic (parasympatholytic) agents such as ipratropium bromide, antihistamines such as chlorpheniramine maleate, beta-agonist bronchodilators, non-steroidal anti-inflammatory drugs, camphor, menthol, *Echinacea*, mast cell stabilizers such as cromolyn sodium, topical nasal steroids such as fluticasone propionate, budenoside, mometasone, triamcinolone, and dexamethasone and zinc salts.

In any of the preceding methods, uses or therapeutic compositions of the invention, the sample may be collected using sterile swabs, sterile gauze, nasal washing, suction tube or a balloon catheter.

For the detecting step in any of the preceding methods of the invention, the biomarker may be detected using a monoclonal antibody. In addition, an immunoassay may be used to detect the biomarker of interest in any of the preceding methods of the invention.

In any of the preceding methods of the invention, the sample may be collected with a device comprising a substrate presenting antibodies specific for the biomarkers of interest, such as a balloon catheter wherein the substrate is threaded into the suction port of the catheter.

An another aspect of the invention provides for immunoassays for detecting the presence of a pathogenic bacteria in the upper respiratory tract of a subject comprising the steps of a) obtaining a sample of secretions from the upper respiratory tract of the subject using a device comprising antibodies specific for at least one biomarker associated with the presence of a pathogenic bacteria in the upper respiratory tract of the subject; b) detecting the presence of at least one biomarker associated with the presence of a pathogenic bacteria in the upper respiratory tract of the subject to generate a protein profile; c) comparing the protein profile with a reference protein profile, wherein the reference protein profile identifies a pathogenic bacteria; and d) determining whether the protein profile of the sample associates to the reference protein profile, wherein association is indicative of the presence of the pathogenic bacteria in the upper respiratory tract of the subject.

The term "immunoassay" is a laboratory approach to directly or indirectly detect protein or peptide in fluid, e.g. biological fluid, by use of an immunological reaction between an antigen and an antibody.

The term "antibody" is synonymous with "immunoglobulin," and includes naturally occurring human antibodies, polyclonal antibodies, and monoclonal antibodies. The term "antibody" is meant to include both the native antibody and biologically active and synthetic derivatives of antibodies, such as, for example, Fab', F(ab")$_2$ or Fv as well as single-domain and single-chain antibodies. A biologically active derivative of an antibody retains the ability to bind an antigen. In particular, the invention provides for methods and immunoassays that use antibodies specific for the biomarkers of interests, such as monoclonal antibodies that specifically bind biomarkers of interest, e.g. OMP P2 and OMP P5.

In addition, the immunoassays described above may further comprising a step of diagnosing the subject with a bacterial infection wherein the presence of the pathogenic bacteria in the upper respiratory tract of the subject is indicative of a bacterial infection.

The invention also provides for any of the preceding immunoassay further comprising the step of administering a therapeutic compound in an amount effective to treat the bacterial infection. Exemplary therapeutic compounds include antibiotics such as penicillin, erythromycin, amoxicillin, thimethoprim-sulfamethoxazole, doxycyline, cefpodoxime, cefuroxime, cefdinir, clarithromycin, azithromycin, levofloxacin, gatifloxacin, and moxifloxacin, alpha-adreneric agonists such as oxymetazoline hydrochloride, anticholinergic (parasympatholytic) agents such as ipratropium bromide, antihistamines such as chlorpheniramine maleate, beta-agonist bronchodilators, non-steroidal anti-inflammatory drugs, camphor, menthol, *Echinacea*, mast cell stabilizers such as cromolyn sodium, topical nasal steroids such as fluticasone propionate, budenoside, mometasone, triamcinolone, and dexamethasone, and zinc salts.

In any of the preceding immunoassays, the pathogenic bacteria detected may be *Haemophilus influenzae, Streptococcus pneumoniae, Moraxella catarrhalis, Staphylococcus aureus, Pseudomonas aeruginosa* or *Stenotrophomonas maltophilia*.

The invention also provides for uses of a therapeutic compound for the preparation of a medicament to reduce or eliminate NTHI bacteria in the upper respiratory tract of a subject or to treat a NTHi infection in the upper respiratory tract of a subject, wherein the presence of NTHi bacterial or a NTHi infection is determined by the presence of at least one biomarker selected from OMP P2 and OMP P5 as determined by any of the preceding In addition, the invention provides for a therapeutic composition for the reduction or elimination of NTHI bacteria in the upper respiratory tract of a subject or for the treatment of NTHI infection in the upper airway of a subject, wherein the presence of NTHi bacteria or NTHI infection is determined by the presence of at least one biomarker selected from OMP P2 and OMP P5 as determined by any of the preceding immunoassays.

In another aspect of the invention, the invention provides for immunoassays for detecting the presence of a nontypeable NTHI bacteria in the upper respiratory tract of a subject comprising the steps of a) obtaining a sample of secretions from the upper respiratory tract of the subject using a device comprising antibodies specific for at least one biomarker associated with the presence of a NTHI bacteria in the upper respiratory tract of the subject, wherein at least one biomarker is OMP P2 or OMP P5; b) detecting the presence of at least one biomarker associated with the presence of a NTHI bacteria in the upper respiratory tract of the subject to generate a protein profile; c) comparing the protein profile with a reference protein profile, wherein the reference protein profile identifies NTHI bacteria; and d) determining whether the protein profile of the sample associates to the reference protein profile, wherein association is indicative of the presence of the NTHI bacteria in the upper respiratory tract of the subject.

The invention also provides for immunoassays for detecting the presence NTHI bacteria in the upper respiratory tract of a subject as described above further comprising a step of diagnosing the subject with a NTHI infection wherein the presence of NTHI bacteria in the upper respiratory tract of the subject is indicative of a NTHI infection.

The invention also provides for any of the preceding immunoassays, which further comprise the step of administering a therapeutic compound in an amount effective to treat the bacterial infection. Exemplary therapeutic compounds include antibiotics such as penicillin, erythromycin, amoxicillin, thimethoprim-sulfamethoxazole, doxycyline, cefpodoxime, cefuroxime, cefdinir, clarithromycin, azithromycin, levofloxacin, gatifloxacin, and moxifloxacin, alpha-adreneric agonists such as oxymetazoline hydrochloride, anticholinergic (parasympatholytic) agents such as ipratropium bromide, antihistamines such as chlorpheniramine maleate, beta-agonist bronchodilators, non-steroidal anti-inflammatory drugs, camphor, menthol, *Echinacea*, mast cell stabilizers such as cromolyn sodium, topical nasal steroids such as fluticasone propionate, budenoside, mometasone, triamcinolone, and dexamethasone, and zinc salts.

In another aspect of the invention, the invention provides for immunoassays for diagnosing a NTHI infection in the upper respiratory tract of a subject comprising the steps of a) obtaining a sample of secretions from the upper respiratory tract of the subject using a device comprising antibodies specific for at least one biomarker associated with the presence of a NTHI in the upper respiratory tract of the subject, wherein the at least one biomarker is OMP P2 or OMP P5; b) detecting the presence of at least one biomarker associated with the presence of a NTHI in the upper respiratory tract of the subject to generate a protein profile; c) comparing the protein profile with a reference protein profile, wherein the reference protein profile identifies NTHI; and d) determining whether the protein profile of the sample associates to the reference protein profile, wherein association is indicative of a NTHI infection in the upper respiratory tract of the subject.

The invention also provides for any of the preceding immunoassays further comprising the step of informing the subject of the presence of a NTHI bacteria or a NTHI infection in the upper respiratory tract of the subject. Exemplary therapeutic compounds include antibiotics such as penicillin, erythromycin, amoxicillin, thimethoprim-sulfamethoxazole, doxycyline, cefpodoxime, cefuroxime, cefdinir, clarithromycin, azithromycin, levofloxacin, gatifloxacin, and moxifloxacin, alpha-adreneric agonists such as oxymetazoline hydrochloride, anticholinergic (parasympatholytic) agents such as ipratropium bromide, antihistamines such as chlorpheniramine maleate, beta-agonist bronchodilators, non-steroidal anti-inflammatory drugs, camphor, menthol, *Echinacea*, mast cell stabilizers such as cromolyn sodium, topical nasal steroids such as fluticasone propionate, budenoside, mometasone, triamcinolone, and dexamethasone, and zinc salts.

In addition, the sample used in any of the preceding immunoassays may be obtained using a sterile swab, sterile gauze, suction tube or a balloon catheter.

In another aspect of the invention, the invention provides for a device for obtaining a sample of secretions from the upper respiratory tract of a subject comprising a substrate presenting antibodies specific for at least one biomarker associated with the presence of a pathogenic bacteria in the upper respiratory tract of the subject.

The invention also provides for devices for carrying out any of the preceding methods of the invention or any of the preceding immunoassays of the invention which is used for obtaining a sample of secretions from the upper respiratory tract of a subject comprising a substrate presenting antibodies specific for biomarkers associated with the presence of a pathogenic bacteria in the upper respiratory tract of the subject.

In any of the preceding devices, the antibodies may be specific for OMP P2 or OMP P5, such as monoclonal antibodies that specifically bind NTHI OMP P2 or monoclonal antibodies that specifically bind NTHI OMP P5.

In another aspect of the invention, the invention provides for kits for carrying out any of the preceding methods or immunoassays. In one embodiment, the kits comprise a substrate presenting antibodies specific for at least one biomarker associated with the presence of a pathogenic bacteria or a bacterial infection in the upper respiratory tract of the subject. In another embodiment, the kits comprise devices for obtaining the sample from the sterile compartments within the upper respiratory tract of the subject and generating a protein profile associated with a pathogenic bacteria or bacterial infection in the upper respiratory tract of the subject. The kits may also comprise antibodies that specifically bind the protein biomarkers of interest and components for immunoassays to detect the protein biomarkers using these antibodies.

DETAILED DESCRIPTION

Figure 1:
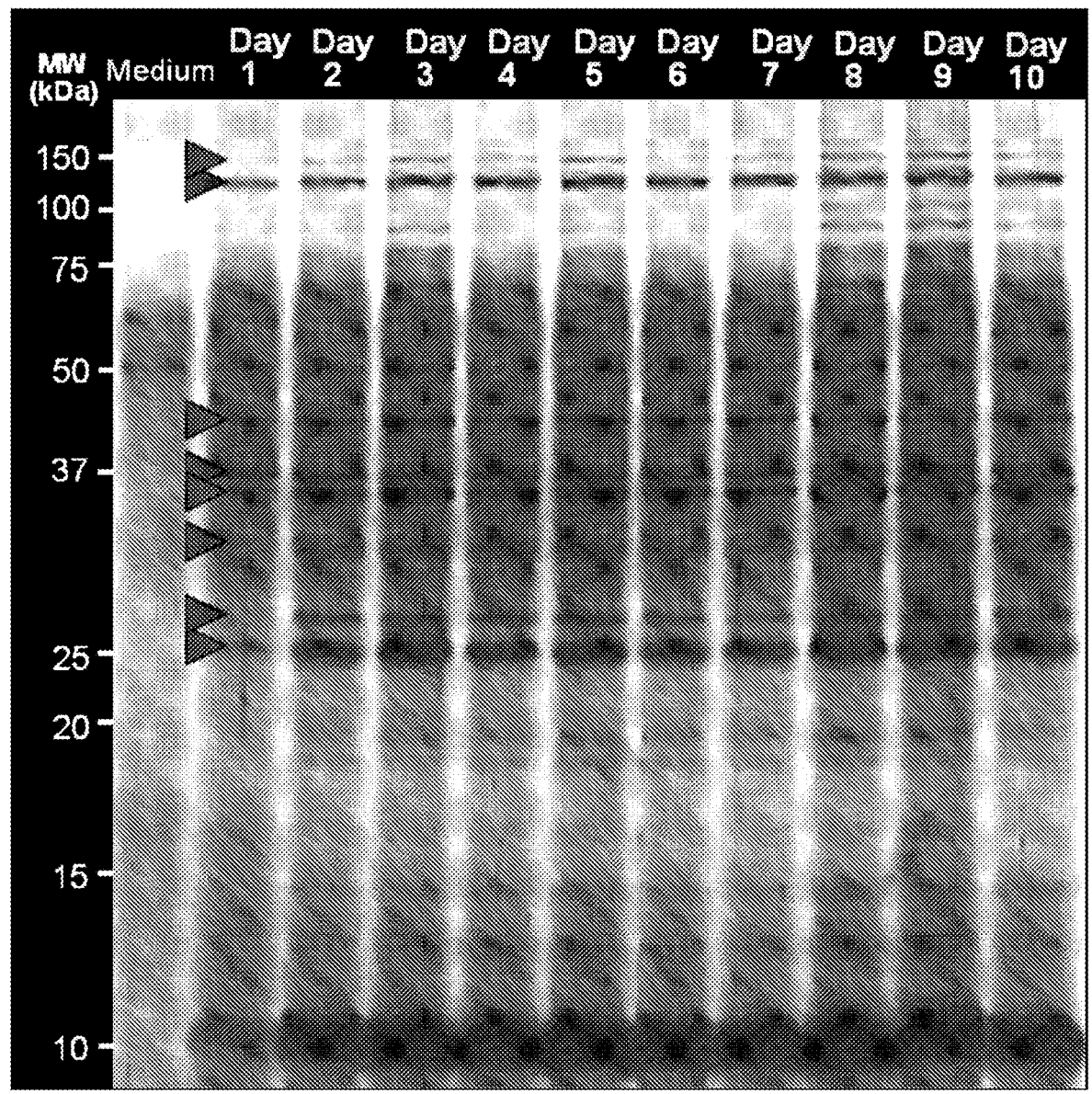
FIG. 1 depicts a silver stain of the distinct protein profile maintained over time in the NTHI biofilm supernatant.

The invention provides for methods with improved sensitivity and specificity for detecting and diagnosing bacterial sinusitis. In particular, the methods of invention comprise antibody-based bacterial detection of proteins within secretions of pathogenic biofilm located within the paranasal sinus cavities. These methods allow for the detection of trace quantities of signature proteins that identify specific bacterial pathogens from typically sterile sites in the paranasal sinus cavities. The methods of the invention provide for the ability to avoid broad-spectrum, empiric antibiotics which are often inappropriately given treat upper viral respiratory infections due to the difficulty in diagnosing bacterial sinusitis with a high sensitivity and high specificity. The methods of the invention are an improvement over typical bacterial cultures because these cultures have very low sensitivity for detecting bacterial biofilms and low specificity for distinguishing between commensal and pathogenic organisms.

The invention also provides for a device that involves delivering a wire through a balloon catheter to the typically sterile paranasal sinus cavities, sampling mucus from these sites, and rapidly detecting the presence of trace quantities of signature proteins that identify specific bacterial pathogens from these typically sterile sites. Upon obtaining the sample, an immunoassay may be run to generate a protein profile that is compared to a reference protein profile generated for the pathogenic bacteria known to cause chronic sinusitis or an infection of the upper respiratory tract.

Biomarkers

The term "biomarker" refers to a naturally occurring molecule, gene, or characteristic by which a particular pathological or physiological process, disease, or the like can be identified or characterized. The term "biomarker" may refer to a protein measured in sample whose concentration reflects the severity or presence of some disease state. Biomarkers may be measured to identify risk for, diagnosis of or progression of a pathological or physiological process, disease or the like. Exemplary biomarkers include proteins, hormones, prohormones, lipids, carbohydrates, DNA, RNA and combinations thereof.

For example, biomarkers for NTHI pathogenic bacteria include outer membrane protein P2 (OMP P2: SEQ ID NO: 1), high molecular weight adhesin 1 (HMW1A; SEQ ID NO: 2), putative periplasmic chelated iron binding proteins (SEQ ID NO: 3), IgA-specific serine endopeptidase (SEQ ID NO: 4), outer membrane protein P5 (OMP P5; SEQ ID NO: 5), galactose-1-phosphate uridylyltransferase (SEQ ID NO: 6), HMWA (SEQ ID NO: 7), phosphate ABC transporter phosphate-binding protein (SEQ ID NO: 8), putative adhesin B precursor FimA (SEQ ID NO: 9), high molecular weight adhesin 2 (HMW2A; SEQ ID NO: 10), outer membrane protein P5 precursor (SEQ ID NO: 11) and outer membrane protein P1 (OMP P1; SEQ ID NO: 12).

The methods of the invention include detecting at least one biomarker, at least two biomarkers, at least three biomarkers, at least four biomarkers, at least five biomarkers or six or more biomarkers of the protein profile of a pathogenic bacteria. Detection of the protein biomarkers includes detecting full length or fragments of the protein biomarkers, including immunogenic or biologically active fragments. In particular, the methods of the invention include detecting at least OMP P2 and OMP 5 to generate a protein profile of NTHI bacteria.

The invention also provides biologically active or immunologically active variants of the amino acid sequences of the present invention; and "substantial equivalents" thereof (e.g., with at least about 65%, at least about 70%, at least about 75%, at least about 80%, at least about 85%, 86%, 87%, 88%, 89%, at least about 90%, 91%, 92%, 93%, 94%, typically at least about 95%, 96%, 97%, more typically at least about 98%, or most typically at least about 99% amino acid identity) that retain biological and/or immunogenic activity. Polypeptides encoded by allelic variants may have a similar, increased, or decreased activity compared to polypeptides encoded by the native polynucleotides.

The present invention further provides isolated polypeptides or peptides encoded by the nucleic acid fragments or by degenerate variants of the nucleic acid fragments. The term "degenerate variant" refers to nucleotide fragments which differ from a native nucleic acid fragment (e.g., an ORF) by nucleotide sequence but, due to the degeneracy of the genetic code, encode an identical polypeptide sequence. Preferred nucleic acid fragments are the ORFs that encode proteins.

The invention also provides for polypeptides with one or more conservative amino acid substitutions that do not affect the biological and/or immunogenic activity of the polypeptide. Alternatively, the polypeptides are contemplated to have conservative amino acids substitutions which may or may not alter biological activity. The term "conservative amino acid substitution" refers to a substitution of a native amino acid residue with a nonnative residue, including naturally occurring and nonnaturally occurring amino acids, such that there is little or no effect on the polarity or charge of the amino acid residue at that position. For example, a conservative substitution results from the replacement of a non-polar residue in a polypeptide with any other non-polar residue. Further, any native residue in the polypeptide may also be substituted with alanine, according to the methods of "alanine scanning mutagenesis". Naturally occurring amino acids are characterized based on their side chains as follows: basic: arginine, lysine, histidine; acidic: glutamic acid, aspartic acid; uncharged polar: glutamine, asparagine, serine, threonine, tyrosine; and non-polar: phenylalanine, tryptophan, cysteine, glycine, alanine, valine, proline, methionine, leucine, norleucine, isoleucine. General rules for amino acid substitutions are set forth in Table 1 below.

TABLE 1

Amino Acid Substitutions

| Original Residues | Exemplary Substitutions | Preferred Substitutions |
| --- | --- | --- |
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asn |
| Gly | Pro, Ala | Ala |
| His | Asn, Gln, Lys, Arg | Arg |
| Ile | Leu, Val, Met, Ala, Phe, | Leu |
| Leu | Norleucine, Ile, Val, Met, | Leu |
| Lys | Arg, 1,4 Diaminobutyric | Arg |
| Met | Leu, Phe, Ile | Leu |
| Phe | Leu, Val, Ile, Ala, Tyr | Arg |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, | Leu |

The polypeptides may be encoded by nucleotide sequences that are substantially equivalent to the polynucleotides encoding the polypeptide biomarkers. Polynucleotides according to the invention can have, e.g., at least 65%, at least 70%, at least 75%, at least 80%, 81%, 82%, 83%, 84%, 85%, 86%, 87%, 88%, or 89%, more typically at least 90%, 91%, 92%, 93%, or 94% and even more typically at least 95%, 96%, 97%, 98% or 99% sequence identity to the native polynucleotide sequences.

Included within the scope of the nucleic acid sequences of the invention are nucleic acid sequence fragments that hybridize under stringent conditions to the nucleotide sequences encoding the polypeptide biomarkers or compliments thereof, which fragment is greater than about 5 nucleotides, preferably 7 nucleotides, more preferably greater than 9 nucleotides and most preferably greater than 17 nucleotides. Fragments of, e.g., 15, 17, or 20 nucleotides or more that are selective for (i.e., specifically hybridize to any one of the polynucleotides of the invention) are contemplated. Probes capable of specifically hybridizing to a polynucleotide can differentiate polynucleotide sequences of the invention from other polynucleotide sequences in the same family of genes or can differentiate genes from other bacterial genes, and are preferably based on unique nucleotide sequences.

The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015M sodium citrate at 65-68° C. or 0.015 M sodium chloride, 0.0015M sodium citrate, and 50% formamide at 42° C. See Sambrook et al., Molecular Cloning: A Laboratory Manual, 2.sup.nd Ed., Cold Spring Harbor Laboratory, (Cold Spring Harbor, N.Y. 1989). More stringent conditions (such as higher temperature, lower ionic strength, higher formamide, or other denaturing agent) may also be used, however, the rate of hybridization will be affected. In instances wherein hybridization of deoxyoligonucleotides is concerned, additional exemplary stringent hybridization conditions include washing in 6×.SSC 0.05% sodium pyrophosphate at 37° C. (for 14-base oligos), 48° C. (for 17-base oligos), 55° C. (for 20-base oligos), and 60° C. (for 23-base oligos).

Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecyl sulfate, $NaDodSO_4$, (SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4, however, at typical ionic strength conditions, the rate of hybridization is nearly independent of pH. See Anderson et al., Nucleic Acid Hybridisation: A Practical Approach, Ch. 4, IRL Press Limited (Oxford, England; 1985). Hybridization conditions can be adjusted by one skilled in the art in order to accommodate these variables and allow DNAs of different sequence relatedness to form hybrids.

The sequences falling within the scope of the present invention are not limited to these specific sequences, but also include allelic and species variations thereof. Preferred computer program methods to determine identity and similarity between two sequences include, but are not limited to, the GCG program package, including GAP (Devereux et al., Nucl. Acid. Res., 12:387, -1984; Genetics Computer Group, University of Wisconsin, Madison, Wis.), BLASTP, BLASTN, and FASTA (Altschul et al., J. Mol. Biol., 215: 403-410, 1990). The BLASTX program is publicly available from the National Center for Biotechnology Information (NCBI) and other sources (BLAST Manual, Altschul et al. NCB/NILM/NIH Bethesda, Md. 20894; Altschul et al., supra). The well known Smith Waterman algorithm may also be used to determine identity.

Methods of Generating Protein Profiles

The methods of the invention involve generating a protein profile of secretion samples obtained from the upper respiratory tract of a subject and generating protein profiles of pathogenic bacteria biofilm supernatants. The known pathogenic bacteria biofilm protein profiles may be used as reference protein profiles for use in the methods of the invention.

Separation of protein of interest from the other members of the protein profile may be accomplished by any number of techniques, such as sucrose gradient centrifugation, aqueous or organic partitioning (e.g., two-phase partitioning), non-denaturing gel electrophoresis, isoelectric focusing gel electrophoresis, capillary electrophoresis, isotachyphoresis, mass spectroscopy, chromatography (e.g., HPLC), polyacrylamide gel electrophoresis (PAGE, such as SDS-PAGE), gel permeation, ion-exchange spin columns, and the like. In these embodiments, SELDI, or other rapid analysis techniques, may be used for monitoring the purification process. Following purification, all potential biomarkers may be characterized by SDS PAGE and mass spectrometry and identified by peptide mapping and/or amino acid sequence analysis.

For example, the protein biomarkers may be separated by size or buoyant density gradient separation method, such as a discontinuous sucrose gradient, that separates the component polypeptides of the sample by the sizes of the complexes in which they participate. Sucrose gradients for the separation of proteins are well known, and may be modified as needed. Such modifications may include the use of a continuous, rather than discontinuous gradient, and different gradient conditions (for instance, different sucrose concentrations or different buffers). The length of the gradient can also be varied, with longer gradients expected to give better overall separation of proteins and protein complexes, and to provide a larger number of fractions that are then each individually analyzed using a denaturing system.

The individual protein biomarkers may be separated by electrophoresis based upon size (e.g., by SDS-PAGE or sizing gel). Other separation techniques may include aqueous two-phase partitioning and non-denaturing agarose gel electrophoresis separation. In other embodiments, separation employs denaturing system such as an isoelectric focusing (IEF) gel, capillary electrophoresis, or isotachyphoresis. Alternatively or additionally, two-dimensional electrophoretic analysis may be used (e.g., Wilkins et al., Proteome Research: New Frontiers in Functional Genomics, Springer-Verlag, Berlin, 1997). Proteins can be visualized on such gels using any of various stains known in the art (e.g., Trypan Blue or SyproRuby dye). Traditional buffering systems can also be used for separating proteins in the component fractionations of the described systems. The temperature, voltage, and amperage at which individual gels are run also can be modified, as can the speed and duration of gradient equilibration and centrifugation.

Purification of protein biomarkers be performed using traditional chromatographic techniques. In an embodiment, high pressure liquid chromatography (HPLC) may be used. Also, a combination of high pressure liquid chromatography (HPLC) and sodium dodecyl sulfate polyacrylamide gel electrophoresis (SDS-PAGE) may be used to purify the protein. The fractions may then be assayed for the protein of interest using SELDI or other methods.

A variety of methods may be used to generate the protein profile such as certain Matrix Assisted Laser Desorption Ionization (MALDI) Mass Spectrometry technology, Surface Enhanced Laser Desorption/Ionization (SELDI) and Protein Chip Mass Spectrometry.

The methods may include steps for analyzing the protein profile. In an embodiment, analysis of the protein profile comprises a statistical analysis and other data manipulation techniques (e.g., signal processing, removal of noise). In some embodiments, techniques for analysis comprise computer statistical and data processing software. For example, analysis of the protein profile may comprise a determination of at least one of the molecular weight (mass), net charge, and or amount of the proteins in the sample.

The method may also comprise the step of comparing the protein profile for the subject's sample to a reference protein profile. In addition to biofilm protein profiles generated for known strains of bacteria, the reference profile may be from a healthy control subject who does not exhibit symptoms of the disease of interest (i.e., a negative control). The reference profile may be from a subject who has a disease of interest (i.e., a positive control). Also, the sample protein profile may be compared to a reference protein profile isolated from the same subject, but at a different point in time (e.g., to monitor progression or remission of the disease). In yet other embodiments, the sample protein profile may be compared to a plurality of a reference protein profiles, as for example, reference profiles generated as diagnostic of a particular disease or disease subtype. In this way, it may be possible to determine whether the sample protein profile matches a particular protein or proteins of interest that are typical of any one disease or disease subtype.

Kits and Devices for Carrying Out the Methods of the Invention

The invention provides for kits for carrying out the methods and immunoassays of the invention. In one embodiment, the kits comprise devices for obtaining the secretion sample from the sterile compartments within the upper respiratory tract of the subject. The kits may also comprise antibodies that specifically bind the protein biomarkers of interest and components for immunoassays to detect the protein biomarkers using these antibodies. In addition, the kits may comprise substrates presenting antibodies specific for the protein biomarkers of interest. Furthermore, the kits may comprise instructions for carrying out the any of the methods or immunoassays of the invention.

In one embodiment, secretions from the upper respiratory tract may be obtained using sterile swabs or gauze. In another embodiment of the invention, the secretion sample may be collected using nasal washing methods. Alternatively, the secretion sample may be collected using a suction tube attached to an electric pump and a catheter inserted into the nasopharynx of the subject.

In another embodiment, the device for obtaining the secretion sample is a modified balloon catheter Seldinger technique that allows for collection of secretions from the sterile compartments within the upper respiratory tract of the subject. The balloon catheter may have a substrate presenting antibodies specific for the protein biomarkers of interest threaded into the catheter. In a further embodiment, a modified distal chip brochoesophagoscope or transnasal esophagoscope may be used in which a substrate presenting antibodies specific for the protein biomarkers of interest is threaded into the suction port of the device.

The invention provides for an immunoassay for detecting at least one biomarker that is specific for a biofilm protein profile for a pathogenic bacteria. For example, antibodies specific for two or more biomarkers within the protein profile are presented or absorbed to a solid substrate, and the secretion sample obtained from the upper airway of the respiratory tract of a subject are contacted with the solid substrate and binding of the antibody to the substrate is detected.

Any type of immunoassay system known in the art may be used to detect the biomarkers of the protein profiles. Exemplary methods include, but not limited to: radioimmunoassays, ELISA assays, sandwich assays, precipitin reactions, gel diffusion precipitin reactions, immunodiffusion assays, agglutination assays, fluorescent immunoassays, protein A immunoassays and immunoelectrophoresis assays and any other methods of generating a protein profile described herein. The immunoassays may be a sandwich assay in which the target analyte (biomarker of interest) is "sandwiched" between a labeled antibody and an antibody immobilized on the solid substrate. The immunoassay is read by observing the presence and amount of antigen-labeled antibody complex bound to the immobilized antibody. Another immunoassay may also be a "competition" type immunoassay, wherein an antibody immobilized on a solid surface is contacted with a sample (e.g., secretions from the upper respiratory tract) containing both an unknown quantity of antigen analyte (biomarker of interest) and with labeled antigen of the same type. The amount of labeled antigen bound on the solid substrate is then determined to provide an indirect measure of the amount of antigen analyte (biomarker of interest) in the sample. Such immunoassays are readily performed in a "dipstick" or other test device format (e.g., a flow-through or migratory dipstick or other test device design) for convenient use. For example, numerous types of dipstick immunoassays assays are described in U.S. Pat. No. 5,656,448.

The immune assays may be carried out on sheets, e.g. strips or sheets of nitrocellulose or polyvinylidene difloride (PVDH) or other membranes, dipstick, wells e.g. 96-well plastic plates, or in tubes.

A device used in the methods and immunoassays of the invention can, for example, provide a color indication when the biomarker of interest is within the secretion sample from the upper respiratory tract of a subject. The device could be used in a clinical setting to quickly determine if a subject has a pathological bacteria or a bacterial infection in the upper respiratory tract. Alternatively, the methods and immunoassays of the present invention may be used in combination with a densitometer or generally a device for measuring light intensity, transmittance, reflection or refraction, or for measuring the wavelength of light as a measure of assay result. The densitometer or other device can provide rapid measurement of the optical density of the substrate within the device that have been contacted with the secretions sample. In one embodiment, a change in color, density, or other parameter can be read by the naked eye.

The invention also may be carried out using a lateral-flow immunoassay which contains a device within the assay to extract the sample for analysis, and antibodies specific for the proteins within the protein profile of a pathogenic bacteria of interest. The invention also provides for a immunoassay device, for example, such as those described in U.S. Pat. Nos. 5,415,994 and 5,763,262, which comprise a protein profile identified for a particular pathogenic bacteria using any of the method of the invention. In particular, the invention provides for colorimetric immunoassays that allow for visual detection of the biomarkers of interest within the secretion sample. Visual detection allows for a rapid result which can be incorporated into a treatment plan for the infection.

A reference or standard protein profile may be used in the methods of the invention to compare the sample protein profile generated by the methods, immunoassays or kits of the invention. The reference or standard protein profile provides the concentration of a biomarker known to be present in the biofilm secretion of a pathogenic bacteria within the upper respiratory tract during an infection. A "calibrator" refers to immunoassays that detect known amounts of biomarkers of interest to generate a calibration curve to quantify the concentration of the biomarker in an unknown biological fluid.

The term "standard" or "reference" refers to immunoassays that measure biomarkers of interest from biological fluids known to be collected from a subject having a bacterial infection of the upper respiratory tract in a suitable quantitative form to control the quality of reagents contained in an immunoassay kit of the present invention. Other aspects and advantages of the present invention will be understood upon consideration of the following illustrative examples.

EXAMPLES

Example 1

Determination of Signature Protein Profile for Pathogenic Bacteria

Supernatants from nontypeable *H. influenzae* (NTHI) biofilm were analyzed to determine the NTHI signature protein profile. NTHI strain 86-028NP was cultured in eight-well chamber slides for 10 days and the resulting supernatants were collected at 24 hours intervals. The proteins in the supernatants collected from NTHI biofilm cultures were separated by SDS-PAGE and silver stain revealed a distinct protein profile maintained over time as shown in FIG. 1.

The proteins isolated from NTHI biofilm supernatants were analyzed by nano-liquid chromatography/tandem mass spectrometry (LC-MS/MS). The molecular weights of the identified proteins were compared to the molecular weights of the known protein profile for the NTHI strain 86-028NP ((Bakaletz et al. *Infection and Immunity*, 56(2): 331-335, 1988), and the identified proteins were scored based on their association to the 86-028NP protein profile using Mascot (Matrix Science, Boston Mass.) according to the manufacturer's instructions. The results of this comparison are set out in Table 2 below. Several NTHI outer membrane proteins (OMPs) were identified (in bold), with predominance of major OMPs (bold italics): high molecular weight adhesins 1 and 2 (HMW1/HMW2), OMP P5, OMP P2, OMP P1, and IgA-protease.

Figure 2:
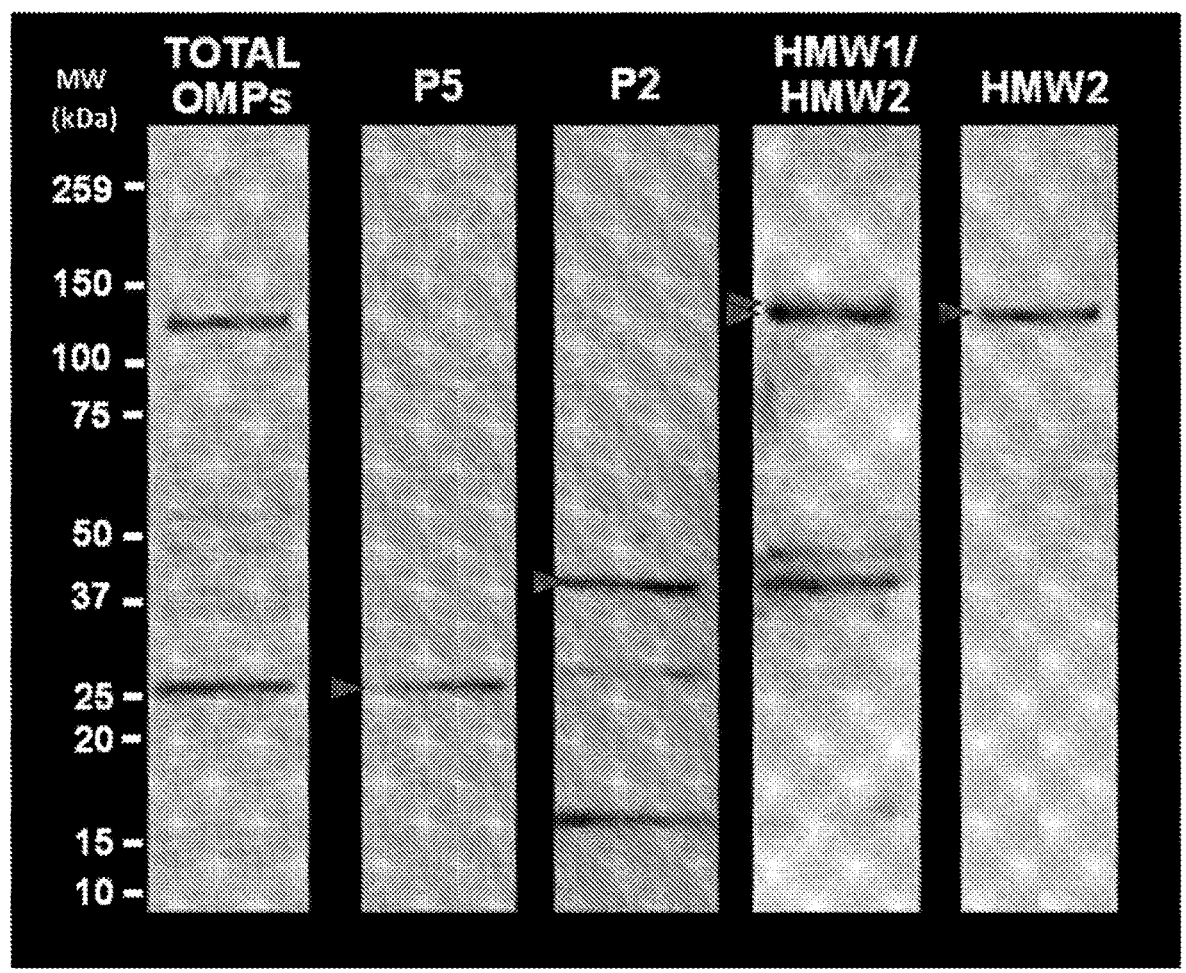
FIG. 2 depicts a Western blot analysis verifying the presence of the NTHI OMPs in NTHI biofilm supernatant.

In order to verify the presence of the NTHI OMPs in NTHI biofilm supernatants, Western blot analysis was carried out with antiserum against total OMPs, OMP P5 and OMP P2 (chinchilla polyclonal antibodies), as well as HMW1 and HMW2 proteins (monoclonal antibodies). This analysis verified the presence of multiple NTHI-specific OMPs in biofilm supernatants (see FIG. 2).

TABLE 2

| IDENTIFIED PROTEIN | Score | Mass (kDa) | Accession # | SEQ ID NO: |
|---|---|---|---|---|
| *Outer membraneprotein P2* | 1227 | 39.9 | gi\|68248747 | 1 |
| *HMW1A*, high molecular weight adhesin 1 | 1205 | 154.5 | gi\|68250281 | 2 |
| putative periplasmic chelated iron binding protein | 1089 | 32.4 | gi\|301169065 | 3 |
| IgA-specific serine endopeptidase | 948 | 197.5 | gi\|68249575 | 4 |
| **Outer membrane*protein P5*** | 886 | 38.4 | gi\|68249712 | 5 |

TABLE 2-continued

| IDENTIFIED PROTEIN | Score | Mass (kDa) | Accession # | SEQ ID NO: |
|---|---|---|---|---|
| galactose-1-phosphate uridylyltransferase | 791 | 34.0 | gi\|145640927 | 6 |
| *HMWA* | 720 | 160.5 | gi\|68249817 | 7 |
| phosphate ABC transporter phosphate-binding protein | 703 | 36.6 | gi\|16273649 | 8 |
| putative adhesin B precursor FimA | 402 | 35.0 | gi\|3003012 | 9 |
| HMW2A, high molecular weight adhesin 2 | 326 | 160.7 | gi\|68249817 | 10 |
| HMWA | 321 | 160.5 | gi\|5929966 | 11 |
| Outer membrane protein P5; Precursor | 283 | 37.7 | gi\|585614 | 12 |
| **Outer membrane*protein P1*** | 215 | 49.7 | gi\|9716607 | 13 |

One example of a signature protein profile of pathogenic NTHI biofilm is OMP P5, OMP P2, HMW1 and HMW2. Therefore, detection of these protein biomarkers in a secretion sample obtained from the upper respiratory tract is indicative of NTHI infection. Precise diagnosis of pathogenic bacterial infection, such as NTHI infection, in patients with upper airway infection will facilitate the selection of appropriate therapy and promote judicious prescription of antibiotics in order to achieve an early recovery in patients and to reduce the emergence of antibiotic-resistant infections in the community.

Example 2

Detection of NTHI Biofilm-Specific Proteins in Paranasal Sinus Infection

In order to determine the protein profile of a human patient suffering from sinusitis, secretion samples are obtained from the upper respiratory tract of the patients. These samples are analyzed as described in Example 1 for the presence of OMP P5, OMP P2, HMW1 and HMW2. The protein profile of the patients is compared with the reference protein profile generated from the supernatants of in vitro NTHI biofilms as described above.

Example 3

Identification of Protein Biomarkers Associated with Other Bacteria Species

The methods described in Example 1 are carried out with the supernatants from biofilms of other pathogenic bacteria species such as *Streptococcus pneumonia, Moraxella catarrhalis, Staphylococcus aureus, Pseudomonas aeruginosa* and *Stenotrophomonas maltophilia*.

Example 4

Figure 3:
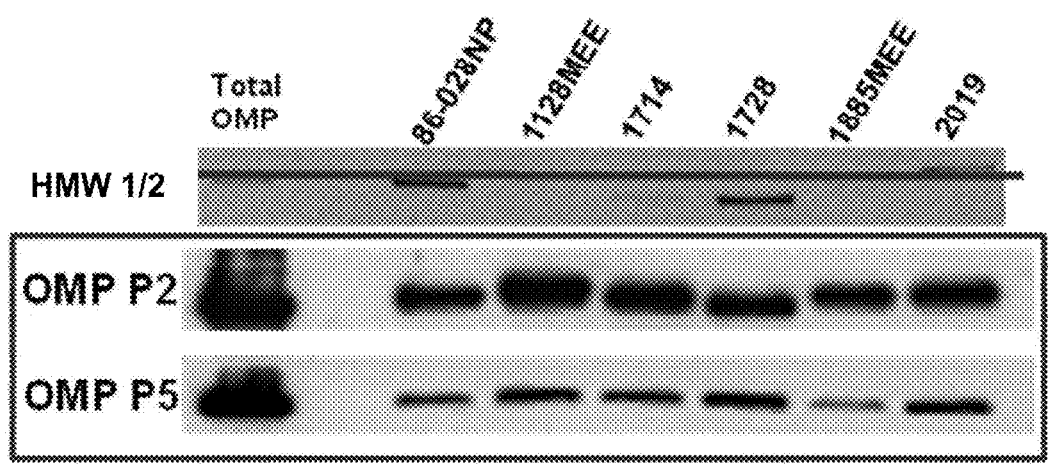
FIG. 3 depicts a Western blot analysis verifying the presence of OMP P2 and OMP P5 in the biofilm supernatant of various strains of NTHI.

Further Analysis of Determination of Signature Protein Profile for Pathogenic Bacteria Supernatants from biofilm obtained from multiple stains of nontypeable *H. influenzae* (NTHI) were analyzed to define the NTHI signature protein profile. NTHI strains 86-028NP, 1128MEE, 1714, 1748, 1885MEE and 2019 were cultured in eight-well chamber slides for 10 days and the resulting supernatants were collected at 24 hours intervals. The proteins in the supernatants collected from NTHI biofilm cultures were separated by SDS-PAGE and silver staining revealed a distinct protein profile maintained over time. FIG. 3 depicts a Western blot using chinchilla anti- OMP P2 or anti-OMP P5 antibodies, which demonstrates that OMP P2 and OMP P5 are present in high levels in the biofilms of all NTHI strains tested.

The proteins isolated from NTHI biofilm supernatants were analyzed by nano-liquid chromatography/tandem mass spectrometry (LC-MS/MS). The molecular weights of the identified proteins were compared to the molecular weights of the known protein profile for the NTHI strain 86-028NP ((Bakaletz et al. *Infection and Immunity,* 56(2): 331-335, 1988), and the identified proteins were scored based on their association to the 86-028NP protein profile using Mascot (Matrix Science, Boston Mass.) according to the manufacturer's instructions. The results of this comparison are set out in Table 3 below. These studies demonstrate that a preferred NTHI biofilm protein profile comprises OMP P2 and OMP P5.

TABLE 3

| Score | Description | Organism |
| --- | --- | --- |
| | P2 Fragment | |
| 2927 | Outer membrane protein P2 | *H. influenzae* |
| 771 | Outer membrane protein P5 | *H. influenzae* |
| 688 | Spermidine/putrescine-binding periplasmic protein 1 | *H. influenzae* |
| 352 | Keratin, type II cytoskeletal 2 epidermal | *Homo sapiens* |
| 335 | Trypsin | *Sus scrofa* |
| 292 | Protein mrp homolog | *H. influenzae* |
| 165 | 3-dehydroquinate synthase | *H. influenzae* |
| 143 | Phenylalanyl-tRNA synthetase alpha chain | *H. influenzae* |
| 105 | Glutamate 5-kinase | *H. influenzae* |
| 100 | Aspartate-semialdehyde dehydrogenase | *H. influenzae* |
| | P5 Fragment | |
| 1512 | Lipoprotein E | *H. influenzae* |
| 1105 | Outer membrane protein P2 | *H. influenzae* |
| 718 | Hybrid peroxiredoxin hyPrx5 | *H. influenzae* |
| 361 | Outer membrane protein P5 | *H. influenzae* |
| 354 | Trypsin OS = Sus scrofa | *Sus scrofa* |
| 255 | 2,3,4,5-tetrahydropyridine-2,6-dicarboxylate N-succinyltransferase | *H. influenzae* |
| 168 | Putative glutamine amidotransferase HI_1037 | *H. influenzae* |
| 167 | Phosphate import ATP-binding protein PstB | *H. influenzae* |
| 124 | Dihydrodipicolinate reductase | *H. influenzae* |
| 118 | Ig kappa chain C region | *M. musculus* |

The isolated proteins were also purified using cationic and gel chromatography. The purified OMP P2 and OMP P5 protein will be used to generate monoclonal antibodies for use in the methods, immunoassays and devices of the invention. It is critical that the antibodies used in the methods, immunoassays and devices of the invention be highly specific. The currently available chinchilla polyclonal antibodies do not exhibit the specificity necessary for carrying out the methods of the invention.

Example 5

Generation of Monoclonal Antibodies

The purified OMP P2 and OMP P5 proteins described in Example 4 are used to generate monoclonal antibodies for use in the methods, immunoassays and devices of the invention using standard techniques well known in the art.

For example, a mouse is immunized intraperitoneally with the purified OMP P2 protein or purified OMP P5 protein. Four days later, the mouse is sacrificed and spleen cells are fused with murine myeloma cells using methods standard in the art. For example, hybridoma technology is described in Kohler et al., *Nature* 256: 495-7 (1975), the human B-cell hybridoma technique is described in Kozbor et al., *Immunol. Today* 4, 72 (1983), the EBV-hybridoma technique to produce human monoclonal antibodies is described in Cole et al. *Monoclonal Antibodies in Cancer Therapy* (1985) Allen R. Bliss, Inc., pages 77-96, and methods of screening combinatorial antibody libraries is described in Huse et al., *Science* 246, 1275 (1989).

The fused cells are cloned in a 96-well plate for single colony selection. Seven to ten days after fusion, culture supernatants from each well with colonies are assayed for the presence of anti-OMP P2 or anti-OMP P5 antibodies. Two to four weeks after cloning, supernatants from single cell colonies are screen for the presence of anti-OMP P2 or anti-OMP P5 antibodies again. Wells with positive reactions are further expanded into larger wells and eventually expanded into flasks to harvest more supernatant for further testing.

Hybridoma cells from the positive clones are injected into pristine mice for production of ascites. The monoclonal antibodies are purified from the ascites, and the specificity of the purified monoclonal antibodies is tested using standard assays known in the art.

Example 6

Immunoassays of the Invention

Anti-OMP P2 and OPM P5 monoclonal antibodies, as described in Example 5, are used to determine the protein profile of a human patient suffering from sinusitis. Secretion samples are obtained from the upper respiratory tract of the patients. These samples are analyzed as described in Example 1 for the presence of at least OMP P5, OMP P2, HMW1 or HMW2. The protein profile of the patients is compared with the reference protein profile generated from the supernatants of in vitro NTHI biofilms as described above The sensitivity and specificity parameters for the use of anti-OMP P2 and anti-OPM P5 monoclonal antibodies, as described in Example 5, are determined against a gold-standard real-time PCR assay using hpd as a primer for the detection of nontypeable *Haemophilus influenzae* that has been shown to be 100% specific and sensitive for the detection of NTHI strains 86-028NP, 1128MEE, 1714, 1748, 1885MEE and 2019 and several clinical isolates of *Moraxella catarrhalis.*

Numerous modifications and variations in the practice of the invention are expected to occur to those of skill in the art upon consideration of the presently preferred embodiments thereof. Consequently, the only limitation which should be placed upon the scope of the invention are those which appear in the appended claims.

What is claimed:

1. A method of detecting the presence of a pathological bacteria in an upper respiratory tract of a subject, the method comprising:
   contacting at least a portion of a sample of secretions from the upper respiratory tract of the subject with a flow-through or a migratory dipstick assay device;
   detecting the presence of an outer membrane protein (OMP) from the pathological bacteria by contacting the sample with antibodies specific for the OMP, wherein the pathological bacteria is nontypeable *Haemophilus influenzae* (NTHI), *Streptococcus pneumoniae, Moraxella catarrhalis, Staphylococcus aureus, Pseudomonas aeruginosa*, or *Stenotrophomonas maltophilia*.

2. The method of claim 1, wherein the flow-through or a migratory dipstick assay device comprises a substrate onto which antibodies specific for the outer membrane protein (OMP) have been immobilized.

3. The method of claim 1, further comprising inserting a collection device into the patient's respiratory tract to obtain the sample of secretions from the respiratory tract of the subject.

4. The method of claim 3, wherein inserting the collection device into the patient's upper respiratory tract comprises inserting a swab.

5. The method of claim 1, further comprising administering a therapeutic compound to the subject to reduce or eliminate the NTHI bacteria in the upper respiratory tract of the subject to treat one or more of: Otitis media, bronchitis, or pharyngitis.

6. The method of claim 1, wherein the OMP is selected from the group consisting of: high molecular weight adhesin 1 (HMW1), high molecular weight adhesin 2 (HMW2), outer membrane protein 5 (OMP P5), outer membrane protein P2 (OMP P2), IgA-protease, putative periplasmic chelated iron binding proteins, IgA-specific serine endopeptidase, galactose-1-phosphate uridylyltransferase, HMWA, phosphate ABC transporter phosphate-binding protein, putative adhesin B precursor FimA, and outer membrane protein P1 (OMP P1).

7. The method of claim 1, wherein the OMP comprises high molecular weight adhesin 1 (HMW1).

8. The method of claim 1, wherein the OMP comprises high molecular weight adhesin 2 (HMW2).

9. The method of claim 1, wherein the OMP comprises IgA-protease.

10. A method of detecting the presence of a pathological bacteria in an upper respiratory tract of a subject, the method comprising:
    contacting a sample of secretions from the upper respiratory tract of the subject with a substrate onto which antibodies specific for an outer membrane protein (OMP) from the pathological bacteria; and
    detecting the antibodies specific for an OMP,
    wherein the pathological bacteria is nontypeable *Haemophilus influenzae* (NTHI) *Streptococcus pneumoniae, Moraxella catarrhalis, Staphylococcus aureus, Pseudomonas aeruginosa*, or *Stenotrophomonas maltophilia*.

11. The method of claim 10, further comprising inserting a collection device into the patient's upper respiratory tract to obtain the sample of secretions from the respiratory tract of the subject.

12. The method of claim 11, wherein inserting the collection device into the patient's upper respiratory tract comprises inserting a swab.

13. The method of claim 10, wherein contacting the sample comprises contacting the sample with a flow-through or migratory dipstick assay device including the substrate.

14. The method of claim 10, further comprising administering a therapeutic compound to the subject to reduce or eliminate the NTHI bacteria in the upper respiratory tract of the subject to treat one or more of: Otitis media, bronchitis, or pharyngitis.

15. The method of claim 10, wherein the OMP is selected from the group consisting of: high molecular weight adhesin 1 (HMW1), high molecular weight adhesin 2 (HMW2), outer membrane protein 5 (OMP P5), outer membrane protein P2 (OMP P2), IgA-protease, putative periplasmic chelated iron binding proteins, IgA-specific serine endopeptidase, galactose-1-phosphate uridylyltransferase, HMWA, phosphate ABC transporter phosphate-binding protein, putative adhesin B precursor FimA, and outer membrane protein P1 (OMP P1).

16. The method of claim 10, wherein the OMP comprises high molecular weight adhesin 1 (HMW1).

17. The method of claim 10, wherein the OMP comprises high molecular weight adhesin 2 (HMW2).

18. The method of claim 10, wherein the OMP comprises IgA-protease.

19. A method of detecting the presence of a pathological bacteria in an upper respiratory tract of a subject, the method comprising:
   contacting a sample of secretions from the upper respiratory tract of the subject with a substrate onto which antibodies specific for an outer membrane protein (OMP) from the pathological bacteria;
   contacting the sample with labeled antibodies specific for the at least one biomarker associated with the presence of a pathological bacteria; and
   detecting the labeled antibody,
   wherein the pathological bacteria is nontypeable *Haemophilus influenzae* (NTHI), *Streptococcus pneumoniae, Moraxella catarrhalis, Staphylococcus aureus, Pseudomonas aeruginosa,* or *Stenotrophomonas maltophilia*.

* * * * *

UNITED STATES PATENT AND TRADEMARK OFFICE
CERTIFICATE OF CORRECTION

PATENT NO. : 10,725,040 B2  Page 1 of 1
APPLICATION NO. : 16/450476
DATED : July 28, 2020
INVENTOR(S) : Subinoy Das et al.

It is certified that error appears in the above-identified patent and that said Letters Patent is hereby corrected as shown below:

In the Specification

At Column 1, Line 18, replace "R01 DC05847 and KL2RR025754" with "RR025754 and DC005847.".

At Column 1, Line 19, delete "United States" immediately prior to "National".

At Column 1, Line 19-20, delete "United States" immediately prior to "government.".

In the Claims

At Column 75, Line 64, replace "Protein 5" with "Protein P5".

At Column 76, Line 4, replace "Protein 5" with "Protein P5".

Signed and Sealed this
First Day of June, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 13

<210> SEQ ID NO 1

```
<211> LENGTH: 365
<212> TYPE: PRT
<213> ORGANISM: Haemophilus influenzae

<400> SEQUENCE: 1
```

| | | | | | | | | | | | | | | |
|---|---|---|---|---|---|---|---|---|---|---|---|---|---|---|
| Met | Lys | Lys | Thr | Leu | Ala | Ala | Leu | Ile | Val | Gly | Ala | Phe | Ala | Ser |
| 1 | | | | 5 | | | | | 10 | | | | | 15 |
| Ala | Ala | Asn | Ala | Ala | Val | Val | Tyr | Asn | Asn | Glu | Gly | Thr | Asn | Val | Glu |
| | | | 20 | | | | | 25 | | | | | 30 | | |
| Leu | Gly | Gly | Arg | Leu | Ser | Ile | Ala | Glu | Gln | Ser | Asn | Ser | Thr | Ile |
| | | 35 | | | | | 40 | | | | | 45 | | |
| Lys | Asp | Gln | Lys | Gln | His | Gly | Ala | Leu | Arg | Asn | Gln | Ser | Ser | Arg |
| | 50 | | | | | 55 | | | | | 60 | | | |
| Phe | His | Ile | Lys | Ala | Thr | His | Asn | Phe | Gly | Asp | Gly | Phe | Tyr | Ala | Gln |
| 65 | | | | | 70 | | | | | 75 | | | | | 80 |
| Gly | Tyr | Leu | Glu | Thr | Arg | Leu | Val | Ser | Ala | Gln | Ser | Gly | Thr | Glu | Ser |
| | | | | 85 | | | | | 90 | | | | | 95 | |
| Asp | Asn | Phe | Gly | His | Ile | Ile | Thr | Lys | Tyr | Ala | Tyr | Val | Thr | Leu | Gly |
| | | | 100 | | | | | 105 | | | | | 110 | | |
| Asn | Lys | Ala | Leu | Gly | Glu | Val | Lys | Leu | Gly | Arg | Ala | Lys | Thr | Ile | Ala |
| | | 115 | | | | | 120 | | | | | 125 | | | |
| Asp | Gly | Ile | Thr | Ser | Ala | Glu | Asp | Lys | Glu | Tyr | Gly | Val | Leu | Asn | Asn |
| | 130 | | | | | 135 | | | | | 140 | | | | |
| Ser | Lys | Tyr | Ile | Pro | Thr | Asn | Gly | Asn | Thr | Val | Gly | Tyr | Thr | Phe | Lys |
| 145 | | | | | 150 | | | | | 155 | | | | | 160 |
| Gly | Ile | Asp | Gly | Leu | Val | Leu | Gly | Ala | Asn | Tyr | Leu | Leu | Ala | Gln | Glu |
| | | | | 165 | | | | | 170 | | | | | 175 | |
| Arg | His | Lys | Tyr | Thr | Thr | Ala | Ala | Gly | Thr | Arg | Ala | Val | Thr | Val | Ala |
| | | | 180 | | | | | 185 | | | | | 190 | | |
| Gly | Glu | Val | Tyr | Pro | Gln | Lys | Ile | Ser | Asn | Gly | Val | Gln | Val | Gly | Ala |
| | | 195 | | | | | 200 | | | | | 205 | | | |
| Lys | Tyr | Asp | Ala | Asn | Asn | Ile | Ile | Ala | Gly | Ile | Ala | Tyr | Gly | Arg | Thr |
| | 210 | | | | | 215 | | | | | 220 | | | | |
| Asn | Tyr | Arg | Glu | Asp | Ile | Val | Asp | Pro | Asp | Leu | Gly | Lys | Lys | Gln | Gln |
| 225 | | | | | 230 | | | | | 235 | | | | | 240 |
| Val | Asn | Gly | Ala | Leu | Ser | Thr | Leu | Gly | Tyr | Arg | Phe | Ser | Asp | Leu | Gly |
| | | | | 245 | | | | | 250 | | | | | 255 | |
| Leu | Leu | Val | Ser | Leu | Asp | Ser | Gly | Tyr | Ala | Lys | Thr | Lys | Asn | Tyr | Lys |
| | | | 260 | | | | | 265 | | | | | 270 | | |
| Asp | Lys | His | Glu | Lys | Ser | Tyr | Phe | Val | Ser | Pro | Gly | Phe | Gln | Tyr | Glu |
| | | 275 | | | | | 280 | | | | | 285 | | | |
| Leu | Met | Glu | Asp | Thr | Asn | Val | Tyr | Gly | Asn | Phe | Lys | Tyr | Glu | Arg | Asp |
| | 290 | | | | | 295 | | | | | 300 | | | | |
| Ser | Val | Asp | Gln | Gly | Lys | Lys | Thr | Arg | Glu | Gln | Ala | Val | Leu | Phe | Gly |
| 305 | | | | | 310 | | | | | 315 | | | | | 320 |
| Val | Asp | His | Lys | Leu | His | Lys | Gln | Val | Leu | Thr | Tyr | Ile | Glu | Gly | Ala |
| | | | | 325 | | | | | 330 | | | | | 335 | |
| Tyr | Ala | Arg | Thr | Arg | Thr | Thr | Glu | Gln | Ala | Lys | Gly | Val | Lys | Thr | Glu |
| | | | 340 | | | | | 345 | | | | | 350 | | |
| Lys | Glu | Lys | Ser | Val | Gly | Val | Gly | Leu | Arg | Val | Tyr | Phe | | | |
| | | | 355 | | | | | 360 | | | | | 365 | | |

```
<210> SEQ ID NO 2
<211> LENGTH: 1492
<212> TYPE: PRT
```

<213> ORGANISM: Haemophilus influenzae

<400> SEQUENCE: 2

```
Met Asn Lys Ile Tyr Arg Leu Lys Phe Ser Lys Arg Leu Asn Ala Leu
1               5                   10                  15

Val Ala Val Ser Glu Leu Thr Arg Gly Cys Asp His Ser Thr Glu Lys
            20                  25                  30

Gly Ser Glu Lys Pro Val Arg Thr Lys Val Arg His Leu Ala Leu Lys
        35                  40                  45

Pro Leu Ser Ala Ile Leu Leu Ser Leu Gly Met Ala Ser Ile Pro Gln
    50                  55                  60

Ser Val Leu Ala Ser Gly Leu Gln Gly Met Ser Val Val His Gly Thr
65                  70                  75                  80

Ala Thr Met Gln Val Asp Gly Asn Lys Thr Thr Ile Arg Asn Ser Val
                85                  90                  95

Asn Ala Ile Ile Asn Trp Lys Gln Phe Asn Ile Asp Gln Asn Glu Met
            100                 105                 110

Val Gln Phe Leu Gln Glu Ser Ser Asn Ser Ala Val Phe Asn Arg Val
        115                 120                 125

Thr Ser Asp Gln Ile Ser Gln Leu Lys Gly Ile Leu Asp Ser Asn Gly
    130                 135                 140

Gln Val Phe Leu Ile Asn Pro Asn Gly Ile Thr Ile Gly Lys Asp Ala
145                 150                 155                 160

Ile Ile Asn Thr Asn Gly Phe Thr Ala Ser Thr Leu Asp Ile Ser Asn
                165                 170                 175

Glu Asn Ile Lys Ala Arg Asn Phe Thr Leu Gln Thr Lys Asp Lys
            180                 185                 190

Ala Leu Ala Glu Ile Val Asn His Gly Leu Ile Thr Val Gly Lys Asp
        195                 200                 205

Gly Ser Val Asn Leu Ile Gly Gly Lys Val Lys Asn Glu Gly Val Ile
    210                 215                 220

Ser Val Asn Gly Gly Ser Ile Ser Leu Leu Ala Gly Gln Lys Ile Thr
225                 230                 235                 240

Ile Ser Asp Ile Ile Asn Pro Thr Ile Thr Tyr Ser Ile Ala Ala Pro
                245                 250                 255

Glu Asn Glu Ala Ile Asn Leu Gly Asp Ile Phe Ala Lys Gly Gly Asn
            260                 265                 270

Ile Asn Val Arg Ala Ala Asn Ile Arg Asn Gln Gly Lys Leu Ser Ala
        275                 280                 285

Asp Ser Val Ser Lys Asp Lys Ser Gly Asn Ile Val Leu Ser Ala Lys
    290                 295                 300

Glu Gly Glu Ala Glu Ile Gly Gly Val Ile Ser Ala Gln Asn Gln Gln
305                 310                 315                 320

Ala Lys Gly Gly Lys Leu Met Ile Thr Gly Asp Lys Val Thr Leu Lys
                325                 330                 335

Thr Gly Ala Val Ile Asp Leu Ser Gly Lys Glu Gly Glu Thr Tyr
            340                 345                 350

Leu Gly Gly Asp Glu Arg Gly Glu Gly Lys Asn Gly Ile Gln Leu Ala
        355                 360                 365

Lys Lys Thr Ser Leu Glu Lys Gly Ser Thr Ile Asn Val Ser Gly Lys
    370                 375                 380

Glu Lys Gly Gly Arg Ala Ile Val Trp Gly Asp Ile Ala Leu Ile Asp
385                 390                 395                 400
```

-continued

Gly Asn Ile Asn Ala Gln Gly Lys Asp Ile Ala Lys Thr Gly Gly Phe
                    405                 410                 415
Val Glu Thr Ser Gly His Tyr Leu Ser Ile Gly Asn Asp Ala Ala Val
            420                 425                 430
Glu Ala Lys Glu Trp Leu Leu Asp Pro Asp Asn Val Thr Ile Ser Asn
        435                 440                 445
Gly Asn Asp Asp Gln Ser Gln Leu Lys Asp Asp Arg Gly Asp Ser Pro
    450                 455                 460
Asn Lys Ile Leu Ala Asp Asn Lys His Thr Val Asn Asn Lys Thr Leu
465                 470                 475                 480
Ser Thr Ala Leu Ala Lys Gly Ile Gly Val Asn Ile Ser Ala Lys Lys
                485                 490                 495
Lys Val Asn Val Thr Ala Asp Ile Asn Val His Asn Gly Thr Leu Thr
            500                 505                 510
Leu His Ser Glu Gln Gly Gly Val Glu Ile Asn Gly Asp Ile Thr Ser
        515                 520                 525
Glu Gln Asn Gly Asn Leu Thr Ile Lys Ala Gly Ser Trp Val Asp Val
    530                 535                 540
His Lys Asn Ile Thr Ile Gly Met Gly Phe Leu Asn Ile Thr Ala Gly
545                 550                 555                 560
Gly Ser Val Ala Phe Glu Lys Ala Gly Gly Asp Lys Gly Arg Ala Ala
                565                 570                 575
Ser Asp Ala Lys Ile Val Ala Gln Gly Val Ile Thr Ala Gly Ser Gly
            580                 585                 590
Gln Asp Phe Arg Phe Asn Asn Val Ser Leu Asn Gly Thr Gly Arg Gly
        595                 600                 605
Leu Lys Phe Ile Thr Ala Lys Gly Asn Lys Gly Asn Phe Ser Ala Lys
    610                 615                 620
Phe Asp Gly Val Leu Asn Ile Ser Gly Asn Ile Ser Ile Asn His Thr
625                 630                 635                 640
Ala Asn Asn Gln Leu Ser Tyr Phe His Arg Gln Gly Tyr Thr Tyr Trp
                645                 650                 655
Asn Leu Thr Gln Leu Asn Val Asp Ser Asp Ser Ser Phe Ser Leu Thr
            660                 665                 670
Ser Ile Lys Asp Ala Ile Lys Val Gly Gly Tyr Asp Asn Ala Lys Asp
        675                 680                 685
Lys Lys Asn Thr Gly Gly Ile Gly Phe Thr Arg Asp Thr Ile Phe Asn
    690                 695                 700
Val Lys Gln Gly Ala Arg Val Asp Ile Ser Tyr Thr Leu Pro Ile Ser
705                 710                 715                 720
Pro Val Lys Asn Ser Arg Ile Ala Ala Val Asn Phe Asp Gly Asn Ile
                725                 730                 735
Thr Val Lys Gly Gly Val Val Asn Leu Lys Phe Asn Ala Leu Ser
            740                 745                 750
Asn Asn Tyr Lys Thr Pro Gly Val Asn Ile Ser Ser Arg Phe Ile Asn
        755                 760                 765
Val Thr Glu Gly Ser Gln Leu Asn Ile Thr Gly Ser Met Pro Ser Thr
    770                 775                 780
Thr Leu Phe Asn Val Ala Asn Asp Leu Ile Ile Asn Ala Thr Asn Ser
785                 790                 795                 800
Phe Val Ser Ile Lys Glu Ile Glu Gly Thr Asp Thr His Leu Asp Thr
                805                 810                 815
Gly Leu Lys Val Asn Gly Asn Val Thr Ile Lys Gly Gly Asn Val Thr

-continued

```
                820                 825                 830
Leu Gly Ser Asn Lys Ala Lys Thr Lys Phe Asp Lys Asn Val Thr Val
                835                 840                 845
Glu Lys Gly Ala Asn Leu Thr Leu Ala Ser Ala Asn Phe Gly Asn His
    850                 855                 860
Lys Gly Ala Leu Thr Val Ala Gly Asn Ile Asn Thr Gln Gly Lys Leu
865                 870                 875                 880
Val Ala Thr Gly Asp Thr Ile Asp Val Ser Gly Asp Phe Thr Val Gly
                885                 890                 895
Asn Asp Ala Thr Phe Asn Gly Asn Thr Asn Asn Leu Asn Ile Thr
                900                 905                 910
Gly Asn Phe Thr Asn Asn Gly Thr Ser Ile Ile Asp Val Lys Lys Gly
                915                 920                 925
Ala Ala Lys Leu Gly Asn Ile Thr Asn Glu Gly Ser Leu Asn Ile Thr
            930                 935                 940
Thr His Ala Asn Thr Asn Gln Lys Thr Ile Thr Gly Asn Ile Thr
945                 950                 955                 960
Asn Lys Lys Gly Asp Leu Asn Ile Arg Asp Asn Lys Asn Asn Ala Glu
                965                 970                 975
Ile Gln Ile Gly Gly Asn Ile Ser Gln Lys Glu Gly Asn Leu Thr Ile
                980                 985                 990
Ser Ser Asp Lys Val Asn Ile Thr Lys Gln Ile Thr Ile Lys Ala Gly
            995                 1000                1005
Val Asn Gly Glu Asn Ser Asp  Ser Gly Thr Glu Asn  Asn Ala Asn
    1010                1015                1020
Leu Thr Ile Lys Thr Lys Thr  Leu Glu Leu Thr Asn  Asn Leu Asn
    1025                1030                1035
Ile Ser Gly Phe His Lys Ala  Glu Ile Thr Ala Lys  Asp Asn Ser
    1040                1045                1050
Asp Leu Ile Ile Gly Lys Ala  Ser Ser Asp Ser Gly  Asn Ala Gly
    1055                1060                1065
Ala Gln Lys Val Ile Phe Asp  Lys Val Lys Asp Ser  Lys Ile Ser
    1070                1075                1080
Ala Gly Asn His Asn Val Thr  Leu Asn Ser Glu Val  Glu Thr Ser
    1085                1090                1095
Asn Gly Asn Ser Asn Ala Ala  Gly Asp Ser Asn Gly  Asn Asn Ala
    1100                1105                1110
Gly Leu Thr Ile Ser Ala Lys  Asp Val Ala Val Asn  Asn Asn Ile
    1115                1120                1125
Thr Ser His Lys Thr Ile Asn  Ile Ser Ala Thr Thr  Gly Asn Val
    1130                1135                1140
Thr Thr Lys Glu Gly Thr Thr  Ile Asn Ala Thr Thr  Gly Gly Val
    1145                1150                1155
Glu Val Thr Ala Lys Thr Gly  Asp Ile Lys Gly Gly  Ile Glu Ser
    1160                1165                1170
Lys Ser Gly Gly Val Thr Leu  Thr Ala Thr Gly Asp  Thr Leu Ala
    1175                1180                1185
Val Gly Asn Ile Ser Gly Asn  Thr Val Ser Val Thr  Ala Asn Ser
    1190                1195                1200
Gly Thr Leu Thr Thr Lys Ala  Asp Ser Thr Ile Lys  Gly Thr Gly
    1205                1210                1215
Ser Val Thr Thr Leu Ser Gln  Ser Gly Asp Ile Gly  Gly Thr Ile
    1220                1225                1230
```

```
Ser Gly Lys Thr Val Ser Val Thr Ala Thr Thr Asp Ser Leu Thr
    1235                1240                1245

Val Lys Gly Gly Ala Lys Ile Asn Ala Thr Glu Gly Thr Ala Thr
    1250                1255                1260

Leu Thr Ala Ser Ser Gly Lys Leu Thr Thr Glu Ala Ser Ser Ser
    1265                1270                1275

Ile Thr Ser Ala Lys Gly Gln Val Asp Leu Ser Ala Arg Asp Gly
    1280                1285                1290

Asn Ile Gly Gly Ser Ile Asn Ala Ala Asn Val Thr Leu Asn Thr
    1295                1300                1305

Thr Gly Thr Leu Thr Thr Val Lys Gly Ser Ser Ile Asn Ala Asn
    1310                1315                1320

Ser Gly Thr Leu Val Ile Asn Ala Glu Asp Ala Lys Leu Asp Gly
    1325                1330                1335

Thr Ala Ser Gly Asp Arg Thr Val Val Asn Ala Thr Asn Ala Ser
    1340                1345                1350

Gly Ser Gly Ser Val Thr Ala Val Thr Ser Ser Ser Val Asn Ile
    1355                1360                1365

Thr Gly Asp Leu Ser Thr Ile Asn Gly Leu Asn Ile Ile Ser Lys
    1370                1375                1380

Asn Gly Lys Asn Thr Val Val Leu Lys Gly Ala Glu Ile Asp Val
    1385                1390                1395

Lys Tyr Ile Gln Pro Gly Val Ala Ser Ala Glu Val Ile Glu
    1400                1405                1410

Ala Lys Arg Ala Leu Glu Lys Val Lys Asp Leu Ser Asp Glu Glu
    1415                1420                1425

Arg Glu Thr Leu Ala Lys Leu Gly Val Ser Ala Val Arg Phe Val
    1430                1435                1440

Glu Pro Asn Asn Ala Ile Thr Val Asn Thr Gln Asn Glu Phe Thr
    1445                1450                1455

Thr Arg Pro Ser Ser Gln Val Thr Ile Ser Glu Gly Lys Ala Cys
    1460                1465                1470

Phe Ser Ser Gly Asp Gly Ala Ala Val Cys Thr Asn Val Ala Asp
    1475                1480                1485

Asp Gly Gln Gln
    1490

<210> SEQ ID NO 3
<211> LENGTH: 293
<212> TYPE: PRT
<213> ORGANISM: Haemophilus influenzae

<400> SEQUENCE: 3

Met Arg Asn Ser Phe Lys Ile Met Thr Ala Leu Ala Leu Gly Leu Phe
1               5                   10                  15

Ala Met Gln Ala Asn Ala Lys Phe Lys Val Val Thr Thr Phe Thr Val
                20                  25                  30

Ile Gln Asp Ile Ala Gln Asn Val Ala Gly Asp Ala Ala Thr Val Glu
        35                  40                  45

Ser Ile Thr Lys Pro Gly Ala Glu Ile His Glu Tyr Glu Pro Thr Pro
    50                  55                  60

Lys Asp Ile Val Lys Ala Gln Ser Ala Asp Leu Ile Leu Trp Asn Gly
65                  70                  75                  80

Leu Asn Leu Glu Arg Trp Phe Glu Arg Phe Phe Gln Asn Val Lys Asp
```

```
                85                  90                  95
Lys Pro Ala Val Val Thr Glu Gly Ile Gln Pro Leu Ser Ile Tyr
            100                 105                 110

Glu Gly Pro Tyr Lys Asp Ala Pro Asn Pro His Ala Trp Met Ser Pro
            115                 120                 125

Ser Asn Ala Leu Ile Tyr Ile Glu Asn Ile Lys Asn Ala Leu Val Lys
130                 135                 140

Tyr Asp Pro Gln Asn Ala Ala Val Tyr Glu Lys Asn Ala Ala Asp Tyr
145                 150                 155                 160

Ala Gln Lys Ile Lys Gln Leu Asp Glu Pro Leu Arg Ala Lys Leu Ala
            165                 170                 175

Gln Ile Pro Glu Ala Gln Arg Trp Leu Val Thr Ser Glu Gly Ala Phe
            180                 185                 190

Ser Tyr Leu Ala Lys Asp Tyr Asn Leu Lys Gly Tyr Leu Trp Pro
            195                 200                 205

Ile Asn Ala Glu Gln Gln Gly Thr Pro Gln Gln Val Arg Lys Val Ile
            210                 215                 220

Asp Leu Val Arg Lys Asn Asn Ile Pro Val Val Phe Ser Glu Ser Thr
225                 230                 235                 240

Ile Ser Ala Lys Pro Ala Gln Gln Val Ala Lys Glu Ser Gly Ala Lys
            245                 250                 255

Tyr Gly Gly Val Leu Tyr Val Asp Ser Leu Ser Ala Lys Asn Gly Pro
            260                 265                 270

Val Pro Thr Tyr Ile Asp Leu Leu Asn Val Thr Val Ser Thr Ile Val
            275                 280                 285

Lys Gly Phe Gly Lys
            290

<210> SEQ ID NO 4
<211> LENGTH: 1794
<212> TYPE: PRT
<213> ORGANISM: Haemophilus influenzae

<400> SEQUENCE: 4

Met Leu Asn Lys Lys Phe Lys Leu Asn Phe Ile Ala Leu Thr Val Ala
1               5                   10                  15

Tyr Ala Leu Thr Pro Tyr Thr Glu Ala Ala Leu Val Arg Asn Asp Val
            20                  25                  30

Asp Tyr Gln Ile Phe Arg Asp Phe Ala Glu Asn Lys Gly Lys Phe Ser
        35                  40                  45

Val Gly Ala Thr Asn Val Glu Val Arg Asp Asn Lys Asn Asn Asn Leu
    50                  55                  60

Gly Ser Ala Leu Pro Lys Asp Ile Pro Met Ile Asp Phe Ser Ala Val
65                  70                  75                  80

Asp Val Asp Lys Arg Ile Ala Thr Leu Val Asn Pro Gln Tyr Val Val
                85                  90                  95

Gly Val Lys His Val Gly Asn Gly Val Gly Glu Leu His Phe Gly Asn
            100                 105                 110

Leu Asn Gly Asn Trp Asn Pro Lys Phe Gly Asn Ser Ile Gln His Arg
            115                 120                 125

Asp Val Ser Trp Glu Glu Asn Arg Tyr Tyr Thr Val Glu Lys Asn Asn
        130                 135                 140

Phe Ser Ser Glu Leu Asn Gly Lys Thr Gln Asn Asn Glu Lys Asp Lys
145                 150                 155                 160
```

-continued

Gln Tyr Thr Ser Asn Lys Lys Asp Val Pro Ser Glu Leu Tyr Gly Gln
                165                 170                 175
Ala Leu Val Lys Glu Gln Gln Asn Gln Lys Arg Arg Glu Asp Tyr Tyr
            180                 185                 190
Met Pro Arg Leu Asp Lys Phe Val Thr Glu Val Ala Pro Ile Glu Ala
        195                 200                 205
Ser Thr Thr Ser Ser Asp Ala Gly Thr Tyr Asn Asp Gln Asn Lys Tyr
    210                 215                 220
Pro Ala Phe Val Arg Leu Gly Ser Gly Ser Gln Phe Ile Tyr Lys Lys
225                 230                 235                 240
Gly Ser His Tyr Glu Leu Ile Leu Glu Glu Lys Asn Glu Lys Lys Glu
                245                 250                 255
Ile Ile His Arg Trp Asp Val Gly Gly Asp Asn Leu Lys Leu Val Gly
            260                 265                 270
Asn Ala Tyr Thr Tyr Gly Ile Ala Gly Thr Pro Tyr Lys Val Asn His
        275                 280                 285
Thr Asp Asp Gly Leu Ile Gly Phe Gly Asp Ser Thr Glu Asp His Asn
    290                 295                 300
Asp Pro Lys Glu Ile Leu Ser Arg Lys Pro Leu Thr Asn Tyr Ala Val
305                 310                 315                 320
Leu Gly Asp Ser Gly Ser Pro Leu Phe Val Tyr Asp Lys Ser Lys Glu
                325                 330                 335
Lys Trp Leu Phe Leu Gly Ala Tyr Asp Phe Trp Gly Tyr Lys Lys
            340                 345                 350
Lys Ser Trp Gln Glu Trp Asn Ile Tyr Lys Pro Gln Phe Ala Glu Asn
        355                 360                 365
Ile Leu Lys Lys Asp Ser Ala Gly Leu Leu Lys Gly Asn Thr Gln Tyr
    370                 375                 380
Asn Trp Thr Ser Lys Gly Asn Thr Ser Leu Ile Ser Gly Thr Ser Glu
385                 390                 395                 400
Ser Leu Ser Val Asp Leu Val Asp Asn Lys Asn Leu Asn His Gly Lys
                405                 410                 415
Asn Val Thr Phe Glu Gly Ser Gly Asn Leu Thr Leu Asn Asn Asn Ile
            420                 425                 430
Asp Gln Gly Ala Gly Gly Leu Phe Phe Glu Gly Asp Tyr Glu Val Lys
        435                 440                 445
Gly Thr Ser Glu Asn Thr Thr Trp Lys Gly Ala Gly Ile Ser Val Ala
    450                 455                 460
Glu Gly Lys Thr Val Lys Trp Lys Val His Asn Pro Gln Phe Asp Arg
465                 470                 475                 480
Leu Ala Lys Ile Gly Lys Gly Lys Leu Ile Val Glu Gly Arg Gly Asp
                485                 490                 495
Asn Lys Gly Ser Leu Lys Val Gly Asp Gly Thr Val Val Leu Lys Gln
            500                 505                 510
Gln Thr Thr Thr Gly Gln His Ala Phe Ala Ser Val Gly Ile Val Ser
        515                 520                 525
Gly Arg Ser Thr Val Val Leu Asn Asp Asp Asn Gln Val Asp Pro Asn
    530                 535                 540
Ser Ile Tyr Phe Gly Phe Arg Gly Gly Arg Leu Asp Ala Asn Gly Asn
545                 550                 555                 560
Asn Leu Thr Phe Glu His Ile Arg Asn Ile Asp Asp Gly Ala Arg Leu
                565                 570                 575
Val Asn His Asn Met Thr Asn Ala Ser Asn Ile Thr Ile Thr Gly Ala

-continued

```
                580                 585                 590
Gly Leu Ile Thr Asn Pro Ser Gln Val Thr Ile Tyr Thr Pro Ala Ile
            595                 600                 605

Thr Ala Asp Asp Asn Tyr Tyr Tyr Val Pro Ser Ile Pro Arg Gly
610                 615                 620

Lys Asp Leu Tyr Phe Ser Asn Thr Cys Tyr Lys Tyr Tyr Ala Leu Lys
625                 630                 635                 640

Gln Gly Gly Ser Pro Thr Ala Glu Met Pro Cys Tyr Ser Ser Glu Lys
                645                 650                 655

Ser Asp Ala Asn Trp Glu Phe Met Gly Asp Asn Gln Asn Asp Ala Gln
            660                 665                 670

Lys Lys Ala Met Val Tyr Ile Asn Asn Arg Arg Met Asn Gly Phe Asn
            675                 680                 685

Gly Tyr Phe Gly Glu Glu Ala Thr Lys Ala Asp Gln Asn Gly Lys Leu
            690                 695                 700

Asn Val Thr Phe Ser Gly Lys Ser Asp Gln Asn Arg Phe Leu Leu Thr
705                 710                 715                 720

Gly Gly Thr Asn Leu Asn Gly Glu Leu Lys Val Glu Lys Gly Thr Leu
                725                 730                 735

Phe Leu Ser Gly Arg Pro Thr Pro His Ala Arg Asp Ile Ala Asn Ile
                740                 745                 750

Ser Ser Thr Glu Lys Asp Lys His Phe Ala Glu Asn Asn Glu Val Val
            755                 760                 765

Val Glu Asp Asp Trp Ile Asn Arg Thr Phe Lys Ala Thr Asn Ile Asn
            770                 775                 780

Val Thr Asn Asn Ala Thr Leu Tyr Ser Gly Arg Asn Val Glu Ser Ile
785                 790                 795                 800

Thr Ser Asn Ile Thr Ala Ser Asn Lys Ala Lys Val His Ile Gly Tyr
                805                 810                 815

Lys Ala Gly Asp Thr Val Cys Val Arg Ser Asp Tyr Thr Gly Tyr Val
            820                 825                 830

Thr Cys His Asn Asp Thr Leu Ser Thr Lys Ala Leu Asn Ser Phe Asn
            835                 840                 845

Pro Thr Asn Leu Arg Gly Asn Val Asn Leu Thr Glu Ser Ala Asn Phe
            850                 855                 860

Thr Leu Gly Lys Ala Asn Leu Phe Gly Thr Ile Asn Ser Thr Glu Asn
865                 870                 875                 880

Ser Gln Val Asn Leu Lys Glu Asn Ser His Trp Tyr Leu Thr Gly Asn
                885                 890                 895

Ser Asp Val His Gln Leu Asp Leu Ala Asn Gly His Ile His Leu Asn
            900                 905                 910

Asn Val Ser Asp Ala Thr Lys Glu Thr Lys Tyr His Thr Leu Asn Ile
            915                 920                 925

Ser Asn Leu Ser Gly Asn Gly Ser Phe Tyr Tyr Trp Val Asp Phe Thr
            930                 935                 940

Lys Asn Gln Gly Asp Lys Val Val Thr Lys Ser Ala Lys Gly Thr
945                 950                 955                 960

Phe Thr Leu Gln Val Ala Asn Lys Thr Gly Glu Pro Asn His Asn Glu
                965                 970                 975

Leu Thr Leu Phe Asp Ala Ser Asn Ala Thr Glu Arg Ser Gly Leu Asn
            980                 985                 990

Val Ser Leu Ala Asn Gly Lys Val  Asp Arg Gly Ala Trp  Ser Tyr Thr
            995                 1000                 1005
```

```
Leu Lys Glu Asn Ser Gly Arg Tyr Tyr Leu His Asn Pro Glu Val
    1010                1015            1020

Glu Arg Arg Asn Gln Thr Val Asp Thr Pro Ser Ile Ala Thr Ala
    1025                1030            1035

Asn Asn Met Gln Ala Asp Val Pro Ser Val Ser Asn Asn His Glu
    1040                1045            1050

Glu Thr Ala Arg Val Glu Ala Pro Ile Pro Leu Pro Ala Pro Pro
    1055                1060            1065

Ala Pro Ala Thr Gly Ser Ala Met Ala Asn Glu Gln Pro Glu Thr
    1070                1075            1080

Arg Pro Ala Glu Thr Val Gln Pro Thr Met Glu Asp Thr Asn Thr
    1085                1090            1095

Thr His Pro Ser Gly Ser Glu Pro Gln Ala Asp Thr Thr Gln Ala
    1100                1105            1110

Asp Asp Pro Asn Ser Glu Ser Val Pro Ser Glu Thr Ile Glu Lys
    1115                1120            1125

Val Ala Glu Asn Ser Pro Gln Glu Ser Glu Thr Val Ala Lys Asn
    1130                1135            1140

Glu Gln Lys Ala Thr Glu Thr Thr Ala Gln Asn Asp Glu Val Ala
    1145                1150            1155

Lys Glu Ala Lys Pro Thr Val Glu Ala Asn Thr Gln Thr Asn Glu
    1160                1165            1170

Leu Ala Gln Asn Gly Ser Glu Thr Glu Thr Gln Glu Ala Glu
    1175                1180            1185

Thr Ala Arg Gln Ser Glu Ile Asn Ser Thr Glu Glu Thr Val Val
    1190                1195            1200

Glu Asp Asp Pro Thr Ile Ser Glu Pro Lys Ser Arg Pro Arg Arg
    1205                1210            1215

Ser Ile Ser Ser Ser Ser Asn Asn Ile Asn Leu Ala Gly Thr Glu
    1220                1225            1230

Asp Thr Ala Lys Val Glu Thr Glu Lys Thr Gln Glu Ala Pro Gln
    1235                1240            1245

Val Ala Phe Gln Ala Ser Pro Lys Gln Glu Glu Pro Glu Met Ala
    1250                1255            1260

Lys Gln Gln Glu Gln Pro Lys Thr Val Gln Ser Gln Ala Gln Pro
    1265                1270            1275

Glu Thr Thr Thr Gln Gln Ala Glu Pro Ala Arg Glu Asn Val Ser
    1280                1285            1290

Thr Val Asn Asn Val Lys Glu Ala Gln Pro Gln Ala Lys Pro Thr
    1295                1300            1305

Thr Val Ala Ala Lys Glu Thr Thr Ala Ser Asn Ser Glu Gln Lys
    1310                1315            1320

Glu Thr Ala Gln Pro Val Ala Asn Pro Lys Thr Ala Glu Asn Lys
    1325                1330            1335

Ala Glu Asn Pro Gln Ser Thr Glu Thr Thr Asp Glu Asn Ile His
    1340                1345            1350

Gln Pro Glu Ala His Thr Ala Val Ala Ser Thr Glu Val Val Thr
    1355                1360            1365

Pro Glu Asn Ala Thr Thr Pro Ile Lys Pro Val Glu Asn Lys Thr
    1370                1375            1380

Thr Glu Ala Glu Gln Pro Val Thr Glu Thr Thr Thr Val Ser Thr
    1385                1390            1395
```

```
Glu Asn Pro Val Val Lys Asn Pro Glu Asn Thr Thr Pro Ala Thr
    1400            1405                1410
Thr Gln Ser Thr Val Asn Ser Glu Ala Val Gln Ser Glu Thr Ala
    1415            1420                1425
Thr Thr Glu Ala Val Val Ser Gln Ser Lys Val Thr Ser Ala Glu
    1430            1435                1440
Glu Thr Thr Val Ala Ser Thr Gln Glu Thr Thr Val Asp Asn Ser
    1445            1450                1455
Gly Ser Thr Pro Gln Pro Arg Ser Arg Arg Thr Arg Arg Ser Ala
    1460            1465                1470
Gln Asn Ser Tyr Glu Pro Val Glu Leu His Thr Glu Asn Ala Glu
    1475            1480                1485
Asn Pro Gln Ser Gly Asn Asp Val Ala Thr Gln Leu Val Leu Arg
    1490            1495                1500
Asp Leu Thr Ser Thr Asn Thr Asn Ala Val Ile Ser Asp Ala Met
    1505            1510                1515
Ala Lys Ala Gln Phe Val Ala Leu Asn Val Gly Lys Ala Val Ser
    1520            1525                1530
Gln His Ile Ser Gln Leu Glu Met Asn Asn Glu Gly Gln Tyr Asn
    1535            1540                1545
Val Trp Val Ser Asn Thr Ser Met Lys Glu Asn Tyr Ser Ser Ser
    1550            1555                1560
Gln Tyr Arg His Phe Ser Ser Lys Ser Ala Gln Thr Gln Leu Gly
    1565            1570                1575
Trp Asp Gln Thr Ile Ser Ser Asn Val Gln Leu Gly Gly Val Phe
    1580            1585                1590
Thr Tyr Val Arg Asn Ser Asn Asn Phe Asp Lys Ala Ser Ser Lys
    1595            1600                1605
Asn Thr Leu Ala Gln Ala Asn Leu Tyr Ser Lys Tyr Tyr Met Asp
    1610            1615                1620
Asn His Trp Tyr Leu Ala Val Asp Leu Gly Tyr Gly Asn Phe Gln
    1625            1630                1635
Ser Asn Leu Gln Thr Asn His Asn Ala Lys Phe Ala Arg His Thr
    1640            1645                1650
Ala Gln Phe Gly Leu Thr Ala Gly Lys Ala Phe Asn Leu Gly Asn
    1655            1660                1665
Phe Ala Val Lys Pro Thr Val Gly Val Arg Tyr Ser Tyr Leu Ser
    1670            1675                1680
Asn Ala Asn Phe Ala Leu Ala Lys Asp Arg Ile Lys Val Asn Pro
    1685            1690                1695
Ile Ser Val Lys Thr Ala Phe Ala Gln Val Asp Leu Ser Tyr Thr
    1700            1705                1710
Tyr His Leu Gly Glu Phe Ser Ile Thr Pro Ile Leu Ser Ala Arg
    1715            1720                1725
Tyr Asp Ala Asn Gln Gly Ser Gly Lys Ile Asn Val Asp Arg Tyr
    1730            1735                1740
Asp Phe Ala Tyr Asn Val Glu Asn Gln Gln Gln Tyr Asn Ala Gly
    1745            1750                1755
Leu Lys Leu Lys Tyr His Asn Val Lys Leu Ser Leu Ile Gly Gly
    1760            1765                1770
Leu Thr Lys Ala Lys Gln Ala Glu Lys Gln Lys Thr Ala Glu Val
    1775            1780                1785
Lys Leu Ser Phe Ser Phe
```

1790

<210> SEQ ID NO 5
<211> LENGTH: 359
<212> TYPE: PRT
<213> ORGANISM: Haemophilus influenzae

<400> SEQUENCE: 5

```
Met Lys Lys Thr Ala Ile Ala Leu Val Val Ala Gly Leu Ala Ala
1               5                   10                  15

Ser Val Ala Gln Ala Ala Pro Gln Glu Asn Thr Phe Tyr Ala Gly Val
            20                  25                  30

Lys Ala Gly Gln Gly Ser Phe His Asp Gly Ile Asn Asn Gly Ala
            35                  40                  45

Ile Lys Gln Asn Leu Ser Ser Ala Asn Tyr Gly Tyr Arg Arg Asn Thr
    50                  55                  60

Phe Thr Tyr Gly Val Phe Gly Gly Tyr Gln Ile Leu Asn Gln Asp Asn
65                  70                  75                  80

Phe Gly Leu Ala Ala Glu Leu Gly Tyr Asp Asn Phe Gly Arg Val Lys
                85                  90                  95

Leu Arg Glu Ala Gly Lys Pro Lys Ala Lys His Thr Asn His Gly Ala
            100                 105                 110

His Leu Ser Leu Lys Gly Ser Tyr Glu Val Leu Asp Gly Leu Asp Val
            115                 120                 125

Tyr Gly Lys Ala Gly Val Ala Leu Val Arg Ser Asp Tyr Lys Phe Tyr
            130                 135                 140

Glu Val Ala Asn Gly Thr Arg Asp His Lys Lys Gly Arg His Thr Ala
145                 150                 155                 160

Arg Ala Ser Gly Leu Phe Ala Val Gly Ala Glu Tyr Ala Val Leu Pro
                165                 170                 175

Glu Leu Ala Val Arg Leu Glu Tyr Gln Trp Leu Thr Arg Val Gly Lys
            180                 185                 190

Tyr Arg Pro Gln Asp Lys Pro Asn Thr Ala Ile Asn Tyr Asn Pro Trp
            195                 200                 205

Ile Gly Ser Ile Asn Ala Gly Ile Ser Tyr Arg Phe Gly Gln Gly Glu
    210                 215                 220

Ala Pro Val Val Ala Pro Glu Met Val Ser Lys Thr Phe Ser Leu
225                 230                 235                 240

Asn Ser Asp Val Thr Phe Ala Phe Gly Lys Ala Asn Leu Lys Pro Gln
                245                 250                 255

Ala Gln Ala Thr Leu Asp Ser Val Tyr Gly Glu Ile Ser Gln Val Lys
            260                 265                 270

Ser Ala Lys Val Ala Val Ala Gly Tyr Thr Asp Arg Ile Gly Ser Asp
            275                 280                 285

Ala Phe Asn Val Lys Leu Ser Gln Glu Arg Ala Asp Ser Val Ala Asn
    290                 295                 300

Tyr Phe Val Ala Lys Gly Val Ala Asp Ala Ile Ser Ala Thr Gly
305                 310                 315                 320

Tyr Gly Lys Ala Asn Pro Val Thr Gly Ala Thr Cys Asp Gln Val Lys
                325                 330                 335

Gly Arg Lys Ala Leu Ile Ala Cys Leu Ala Pro Asp Arg Arg Val Glu
            340                 345                 350

Ile Ala Val Asn Gly Thr Lys
            355
```

<210> SEQ ID NO 6
<211> LENGTH: 317
<212> TYPE: PRT
<213> ORGANISM: Haemophilus influenzae

<400> SEQUENCE: 6

Met Leu Ser Thr Val Ala Phe Ala Ile Ala Leu Gly Ser Ala Ser Ala
1               5                   10                  15

Ser Phe Ala Ala Asp Asn Arg Ile Gly Val Thr Ile Tyr Lys Tyr Asp
            20                  25                  30

Asp Asn Phe Met Ser Leu Met Arg Lys Glu Ile Asp Lys Glu Ala Lys
        35                  40                  45

Val Val Gly Gly Ile Lys Leu Leu Met Asn Asp Ser Gln Asn Ala Gln
    50                  55                  60

Ser Ile Gln Asn Asp Gln Val Asp Ile Leu Leu Ser Lys Gly Val Lys
65                  70                  75                  80

Ala Leu Ala Ile Asn Leu Val Asp Pro Ala Ala Pro Thr Ile Ile
                85                  90                  95

Gly Lys Ala Lys Ser Asp Asn Ile Pro Val Val Phe Phe Asn Lys Asp
            100                 105                 110

Pro Gly Ala Lys Ala Ile Gly Ser Tyr Glu Gln Ala Tyr Tyr Val Gly
        115                 120                 125

Thr Asp Pro Lys Glu Ser Gly Leu Ile Gln Gly Asp Leu Ile Ala Lys
    130                 135                 140

Gln Trp Lys Ala Asn Pro Ala Leu Asp Leu Asn Lys Asp Gly Lys Ile
145                 150                 155                 160

Gln Phe Val Leu Leu Lys Gly Glu Pro Gly His Pro Asp Ala Glu Val
                165                 170                 175

Arg Thr Lys Tyr Val Val Glu Glu Leu Asn Ala Lys Gly Ile Gln Thr
            180                 185                 190

Glu Gln Leu Phe Ile Asp Thr Gly Met Trp Asp Ala Ala Met Ala Lys
        195                 200                 205

Asp Lys Val Asp Ala Trp Leu Ser Ser Ser Lys Ala Asn Asp Ile Glu
    210                 215                 220

Val Ile Ile Ser Asn Asn Asp Gly Met Ala Leu Gly Ala Leu Glu Ala
225                 230                 235                 240

Thr Lys Ala His Gly Lys Lys Leu Pro Ile Phe Gly Val Asp Ala Leu
                245                 250                 255

Pro Glu Ala Leu Gln Leu Ile Ser Lys Gly Glu Leu Ala Gly Thr Val
            260                 265                 270

Leu Asn Asp Ser Val Asn Gln Gly Lys Ala Val Val Gln Leu Ser Asn
        275                 280                 285

Asn Leu Ala Gln Gly Lys Ser Ala Thr Glu Gly Thr Lys Met Gly Ile
    290                 295                 300

Lys Arg Pro Cys Cys Thr His Ser Leu Cys Trp Cys Gly
305                 310                 315

<210> SEQ ID NO 7
<211> LENGTH: 1542
<212> TYPE: PRT
<213> ORGANISM: Haemophilus influenzae

<400> SEQUENCE: 7

Met Asn Lys Ile Tyr Arg Leu Lys Phe Ser Lys Arg Leu Asn Ala Leu
1               5                   10                  15

```
Val Ala Val Ser Glu Leu Thr Arg Gly Cys Asp His Ser Thr Glu Lys
             20                  25                  30

Gly Ser Glu Lys Pro Val Arg Thr Lys Val Arg His Leu Ala Leu Lys
         35                  40                  45

Pro Leu Ser Ala Ile Leu Leu Ser Leu Gly Met Ala Ser Ile Pro Gln
     50                  55                  60

Ser Val Leu Ala Ser Gly Leu Gln Gly Met Ser Val Val His Gly Thr
 65                  70                  75                  80

Ala Thr Met Gln Val Asp Gly Asn Lys Thr Thr Ile Arg Asn Ser Val
                 85                  90                  95

Asn Ala Ile Ile Asn Trp Lys Gln Phe Asn Ile Asp Gln Asn Glu Met
             100                 105                 110

Val Gln Phe Leu Gln Glu Asn Asn Ser Ala Val Phe Asn Arg Val
         115                 120                 125

Thr Ser Asp Gln Ile Ser Gln Leu Lys Gly Ile Leu Asp Ser Asn Gly
     130                 135                 140

Gln Val Phe Leu Ile Asn Pro Asn Gly Ile Thr Ile Gly Lys Glu Ala
145                 150                 155                 160

Ile Ile Asn Thr Asn Gly Phe Thr Ala Ser Thr Leu Asp Ile Ser Asn
             165                 170                 175

Glu Asn Ile Lys Ala Arg Asn Phe Thr Leu Glu Gln Thr Lys Asp Lys
         180                 185                 190

Ala Leu Ala Glu Ile Val Asn His Gly Leu Ile Thr Val Gly Lys Asp
     195                 200                 205

Gly Ser Val Asn Leu Ile Gly Gly Lys Val Lys Asn Glu Gly Val Ile
 210                 215                 220

Ser Val Asn Gly Gly Ser Ile Ser Leu Leu Ala Gly Gln Lys Ile Thr
225                 230                 235                 240

Ile Ser Asp Ile Ile Asn Pro Thr Ile Thr Tyr Ser Ile Ala Ala Pro
             245                 250                 255

Glu Asn Glu Ala Ile Asn Leu Gly Asp Ile Phe Ala Lys Gly Gly Asn
         260                 265                 270

Ile Asn Val Arg Ala Ala Thr Ile Arg Asn Lys Gly Lys Leu Ser Ala
     275                 280                 285

Asp Ser Val Ser Lys Asp Lys Ser Gly Asn Ile Ile Leu Ser Ala Lys
 290                 295                 300

Glu Gly Glu Ala Glu Ile Ser Gly Val Ile Ser Ala Gln Asn Gln Gln
305                 310                 315                 320

Ala Lys Gly Gly Lys Leu Met Ile Thr Gly Asp Lys Val Thr Leu Lys
             325                 330                 335

Thr Gly Ala Val Ile Asp Leu Ser Gly Lys Glu Gly Gly Glu Thr Tyr
         340                 345                 350

Leu Gly Gly Asp Glu Arg Gly Glu Gly Lys Asn Gly Ile Gln Leu Ala
     355                 360                 365

Lys Lys Thr Ser Leu Glu Lys Gly Ser Thr Ile Asn Val Ser Gly Lys
 370                 375                 380

Glu Lys Gly Gly Arg Ala Ile Val Trp Gly Asp Ile Ala Leu Ile Asp
385                 390                 395                 400

Gly Asn Ile Asn Ala Gln Gly Ser Asp Ile Ala Lys Thr Gly Gly Phe
             405                 410                 415

Val Glu Thr Ser Gly His Tyr Leu Ser Ile Asp Ser Asn Ala Ile Val
         420                 425                 430

Lys Thr Lys Glu Trp Leu Leu Asp Pro Asp Asn Val Thr Ile Glu Ala
```

```
                435                 440                 445
Pro Ser Leu Ser Arg Ala Asp Thr Asp Ile Ser Ser Glu Phe Pro Ile
450                 455                 460
Gly Asp Gly Thr Glu Asn Ser Pro Lys Lys Asn Ala Asp Lys Thr Ile
465                 470                 475                 480
Leu Thr Asn Glu Thr Ile Ser Asn Phe Leu Gln Asn Ala Lys Val Met
            485                 490                 495
Asn Ile Thr Ala Lys Arg Lys Leu Thr Val Asn Ser Ser Ile Ser Ile
            500                 505                 510
Gly Ser Arg Ser His Leu Ile Leu His Ser Glu Gly Gln Gly Asp Gly
            515                 520                 525
Gly Val Gln Ile Asp Gly Asp Ile Thr Ser Glu Gly Gly Asn Leu Thr
530                 535                 540
Ile Asn Ser Gly Gly Trp Val Asp Val His Lys Asn Ile Thr Leu Gly
545                 550                 555                 560
Thr Gly Phe Leu Asn Ile Thr Ala Gly Gly Ser Val Ala Phe Glu Lys
                565                 570                 575
Gly Gly Asn Asn Ala Arg Asn Ala Thr Asp Ala Gln Ile Thr Ala Gln
            580                 585                 590
Gly Thr Ile Thr Val Asn Lys Asp Asp Lys Gln Phe Arg Phe Asn Asn
            595                 600                 605
Val Ser Ile Asn Gly Thr Gly Glu Gly Leu Lys Phe Ile Ala Asn Gln
610                 615                 620
Asn Asn Phe Thr His Lys Phe Asp Gly Glu Ile Asn Ile Ser Gly Ile
625                 630                 635                 640
Val Thr Ile Asn Gln Thr Thr Lys Lys Asp Ala Lys Tyr Trp His Ala
                645                 650                 655
Ser Lys Asp Ser Tyr Trp Asn Val Ser Ser Leu Thr Leu Asn Asp Asp
            660                 665                 670
Ala Lys Phe Thr Phe Ile Lys Phe Val Asp Ser Gly Ser Asn Ser Gln
            675                 680                 685
Asp Leu Arg Ser Ala Arg Arg Phe Ala Gly Val His Phe Asn Gly
690                 695                 700
Thr Gly Gly Lys Thr Asn Phe Asn Ile Gly Ala Asn Ala Lys Ala Leu
705                 710                 715                 720
Phe Lys Leu Lys Pro Asn Ala Ala Thr Asp Pro Lys Lys Glu Leu Pro
                725                 730                 735
Ile Thr Phe Asn Ala Asn Ile Thr Ala Thr Gly Ser Ser Asp Ser Ser
            740                 745                 750
Val Met Phe Asp Ile His Ala Asn Leu Thr Ser Arg Ala Ala Ser Ile
            755                 760                 765
Asn Met Asp Ser Ile Asn Ile Thr Gly Gly Leu Asp Phe Ser Ile Thr
            770                 775                 780
Ser His Asn Arg Asn Ser Asn Ala Phe Glu Ile Lys Lys Asp Leu Thr
785                 790                 795                 800
Ile Asn Ala Thr Asn Ser Lys Phe Ser Leu Lys Gln Thr Lys Asp Leu
                805                 810                 815
Phe Glu Asn Gln Tyr Thr Gly Asp Ala Ile Asn Ser Arg Asn Leu
            820                 825                 830
Thr Ile Leu Gly Gly Asn Val Thr Leu Gly Gly Glu Asn Ser Ser Ser
            835                 840                 845
Asn Ile Thr Gly Asn Ile Thr Ile Ala Ala Glu Ala Asn Val Thr Leu
            850                 855                 860
```

```
Gln Ala Tyr Ala Asp Asn Ser Ile Lys Gly His Lys Lys Thr Leu
865                 870                 875                 880

Thr Leu Gly Asn Val Ser Thr Ser Gly Asn Leu Ser Leu Thr Gly Ser
            885                 890                 895

Lys Val Glu Val Lys Gly Asp Leu Ala Val Leu Asn Gly Ala Thr Phe
        900                 905                 910

Lys Gly Glu Thr Asn Asp Ser Leu Asn Ile Thr Gly Thr Phe Thr Asn
        915                 920                 925

Asn Gly Thr Ala Asp Ile Asn Ile Lys Arg Gly Val Val Asn Ile Gln
        930                 935                 940

Gly Asp Ile Thr Asn Lys Gly Gly Leu Asn Ile Thr Thr Asn Ala Gln
945                 950                 955                 960

Lys Asn Gln Lys Thr Ile Ile Asn Gly Asn Ile Thr Asn Lys Lys Gly
                965                 970                 975

Asn Leu Asn Ile Thr Asn Asn Gly Asn Asp Thr Glu Ile Gln Ile Gly
                980                 985                 990

Gly Asn Ile Ser Gln Lys Glu Gly Asn Leu Thr Ile Ser Ser Asp Lys
        995                 1000                1005

Val Asn Ile Thr Lys Gln Ile Thr Ile Lys Ala Gly Val Asp Glu
    1010                1015                1020

Lys Asp Ser Ser Ser Ser Thr Ala Ser Asp Ala Asn Leu Thr Ile
    1025                1030                1035

Lys Thr Lys Glu Leu Lys Leu Val Glu Asp Leu Asn Ile Ser Gly
    1040                1045                1050

Phe Asn Lys Ala Glu Ile Thr Ala Lys Asp Gly Ser Asp Leu Thr
    1055                1060                1065

Ile Gly Asn Thr Asn Ser Ala Asp Gly Thr Asn Ala Lys Lys Val
    1070                1075                1080

Thr Phe Asn Gln Val Lys Asp Ser Lys Ile Ser Ala Asn Asp His
    1085                1090                1095

Asn Val Thr Leu Asn Ser Lys Val Glu Thr Ser Gly Asn Thr Asp
    1100                1105                1110

Asn Thr Gly Asp Gly Ser Gly Asn Asn Ala Gly Leu Thr Ile Ala
    1115                1120                1125

Ala Lys Asn Val Glu Val Lys Asn Asn Ile Thr Ser Asn Lys Thr
    1130                1135                1140

Val Asn Ile Thr Ala Ser Glu Lys Leu Thr Thr Lys Ala Asp Ala
    1145                1150                1155

Thr Ile Asn Ala Thr Thr Gly Asn Val Glu Val Thr Ala Lys Thr
    1160                1165                1170

Gly Asp Ile Lys Gly Glu Val Lys Ser Thr Ser Gly Asn Val Asn
    1175                1180                1185

Ile Thr Ala Asn Gly Asp Thr Leu Asn Val Ser Asn Val Ser Gly
    1190                1195                1200

Asn Ala Val Thr Ile Thr Ala Asp Lys Gly Lys Leu Thr Thr Gln
    1205                1210                1215

Glu Ser Ser Thr Ile Ser Gly Thr Glu Ser Val Thr Thr Ser Ser
    1220                1225                1230

Gln Ser Gly Asp Ile Gly Gly Ala Ile Ser Gly Asn Thr Val Ser
    1235                1240                1245

Val Lys Ala Thr Asn Asp Leu Ile Thr Lys Ala Asn Ser Lys Ile
    1250                1255                1260
```

Glu Ala Lys Thr Gly Glu Ala Asn Val Thr Ser Ala Thr Gly Ile
            1265                1270                1275

Ile Gly Gly Thr Ile Ser Gly Asn Thr Val Asn Val Thr Ala Asn
            1280                1285                1290

Thr Gly Ser Leu Thr Ile Lys Gly Gly Ala Lys Val Asp Ala Thr
            1295                1300                1305

Asn Gly Ala Ala Thr Leu Thr Ala Glu Ser Gly Lys Leu Thr Thr
            1310                1315                1320

Gln Ala Gly Ser Thr Ile Thr Ser Asn Asn Gly Gln Thr Thr Leu
            1325                1330                1335

Thr Ala Lys Asp Gly Ser Ile Ala Gly Ser Ile Asp Ala Ala Asn
            1340                1345                1350

Val Thr Leu Asn Thr Thr Gly Thr Leu Thr Thr Val Val Gly Ser
            1355                1360                1365

Ser Ile Asn Ala Asn Glu Gly Thr Leu Val Ile Asn Ala Gln Asp
            1370                1375                1380

Ala Thr Leu Asn Gly Asp Ala Ser Gly Asp Arg Thr Glu Val Asn
            1385                1390                1395

Ala Val Asn Ala Ser Gly Ser Gly Ser Val Thr Ala Val Thr Ser
            1400                1405                1410

Ser Ser Val Asn Ile Thr Gly Asp Leu Ser Thr Ile Asn Gly Leu
            1415                1420                1425

Asn Ile Ile Ser Lys Asn Gly Lys Asn Thr Val Val Leu Lys Gly
            1430                1435                1440

Ala Glu Ile Asp Val Lys Tyr Ile Gln Pro Gly Val Ala Ser Ala
            1445                1450                1455

Glu Glu Val Ile Glu Ala Lys Arg Ala Leu Glu Lys Val Lys Asp
            1460                1465                1470

Leu Ser Asp Glu Glu Arg Glu Thr Leu Ala Lys Leu Gly Val Ser
            1475                1480                1485

Ala Val Arg Phe Val Glu Pro Asn Asn Ala Ile Thr Val Asn Thr
            1490                1495                1500

Gln Asn Glu Phe Thr Thr Arg Pro Ser Ser Gln Val Thr Ile Ser
            1505                1510                1515

Glu Gly Lys Ala Cys Phe Ser Gly Asp Gly Ala Ala Val Cys
            1520                1525                1530

Thr Asn Val Ala Asp Asp Gly Gln Gln
            1535                1540

<210> SEQ ID NO 8
<211> LENGTH: 334
<212> TYPE: PRT
<213> ORGANISM: Haemophilus influenzae

<400> SEQUENCE: 8

Met Lys Lys Lys Ser Tyr Tyr Val Leu Thr Leu Gly Thr Leu Pro Phe
1               5                   10                  15

Ala Gln Ala Asn Ser Ile Thr Gly Ala Gly Ala Ser Phe Pro Tyr Pro
                20                  25                  30

Ile Tyr Ala Lys Trp Ala Ser Leu Tyr Glu Lys Glu Thr Gly Asn Lys
            35                  40                  45

Val Asn Tyr Gln Ser Ile Gly Ser Gly Gly Gly Gln Gln Ile Ile
        50                  55                  60

Ala Lys Thr Val Asp Phe Gly Ala Ser Asp Asp Pro Met Lys Ser Glu
65                  70                  75                  80

Leu Leu Gln Gln His Gln Leu Val Gln Phe Pro Ala Val Ile Gly Gly
            85                  90                  95

Ile Val Pro Val Val Asn Leu Pro Glu Ile Lys Pro Gly Lys Leu Lys
            100                 105                 110

Leu Ser Gly Lys Leu Leu Ala Glu Ile Phe Leu Gly Lys Ile Lys Lys
            115                 120                 125

Trp Asn Asp Pro Asp Leu Val Ala Leu Asn Pro Thr Leu Pro Leu Pro
130                 135                 140

Asn Lys Asn Ile Ile Val Ile His Arg Ser Asp Gly Ser Gly Thr Thr
145                 150                 155                 160

Phe Gly Phe Thr Asn Tyr Leu Ser Lys Ile Ser Asn Asp Trp Lys Asn
                165                 170                 175

Gln Val Gly Glu Gly Lys Ser Val Lys Trp Leu Thr Gly Gln Gly Gly
            180                 185                 190

Lys Gly Asn Glu Gly Val Ala Ser Tyr Val Arg Gln Met Lys Tyr Ser
            195                 200                 205

Ile Gly Tyr Val Glu Tyr Ala Tyr Ala Lys Gln Asn Gln Leu Ala Trp
            210                 215                 220

Ile Ser Leu Gln Asn Gln Ala Gly Gln Phe Val Gln Pro Ser Asn Glu
225                 230                 235                 240

Ser Phe Met Ala Ala Ser His Ala Lys Trp His Glu Lys Ala Gly
                245                 250                 255

Met Gly Val Ile Leu Thr Asn Glu Thr Gly Glu Lys Ser Trp Pro Ile
            260                 265                 270

Thr Ala Ala Ser Phe Ile Leu Asn Lys Tyr Ser Asp Asn Pro Glu
            275                 280                 285

Thr Thr Lys Asn Val Leu Ala Phe Phe Asp Trp Ala Phe Ser Arg Gly
            290                 295                 300

Gln Asp Ala Ala Thr Glu Leu Asp Tyr Val Pro Ile Pro Ala Asp Val
305                 310                 315                 320

Val Ser Thr Ile Lys Ser Gln Trp Lys Thr Glu Leu Lys Gln
                325                 330

<210> SEQ ID NO 9
<211> LENGTH: 311
<212> TYPE: PRT
<213> ORGANISM: Haemophilus influenzae

<400> SEQUENCE: 9

Val Leu Ala Ser Val Lys Pro Leu Gly Phe Ile Asp Ser Ser Ile Ala
1               5                   10                  15

Asp Gly Val Thr Gly Thr Gln Val Leu Val Pro Ala Gly Ala Ser Pro
            20                  25                  30

His Asp Tyr Asn Leu Lys Leu Ser Asp Ile Gln Lys Val Lys Ser Ala
            35                  40                  45

Asp Leu Val Val Trp Ile Gly Glu Asp Ile Asp Ser Phe Leu Asp Lys
        50                  55                  60

Pro Ile Ser Gln Ile Glu Arg Lys Lys Val Ile Thr Ile Ala Asp Leu
65                  70                  75                  80

Ala Asp Val Lys Pro Leu Leu Ser Lys Ala His His Glu His Phe His
                85                  90                  95

Glu Asp Gly Asp His Asp His Asp His Lys Asp Glu His Lys His Asp
            100                 105                 110

His Lys His Asp His Lys His Glu His Lys His Glu His Lys His Asp

```
                 115                 120                 125
His Glu His His Asp His Asp His His Glu Gly Leu Thr Thr Asn Trp
130                 135                 140

His Val Trp Tyr Ser Pro Ala Ile Ser Lys Ile Val Ala Gln Lys Val
145                 150                 155                 160

Ala Asp Lys Leu Thr Ala Gln Phe Pro Asp Lys Lys Ala Leu Ile Ala
                165                 170                 175

Gln Asn Leu Ser Asp Phe Asn Arg Thr Leu Ala Glu Gln Ser Glu Lys
                180                 185                 190

Ile Thr Ala Gln Leu Ala Asn Val Lys Asp Lys Gly Phe Tyr Val Phe
                195                 200                 205

His Asp Ala Tyr Gly Tyr Phe Asn Asp Ala Tyr Gly Leu Lys Gln Thr
210                 215                 220

Gly Tyr Phe Thr Ile Asn Pro Leu Val Ala Pro Gly Ala Lys Thr Leu
225                 230                 235                 240

Ala His Ile Lys Glu Glu Ile Asp Glu His Lys Val Asn Cys Leu Phe
                245                 250                 255

Ala Glu Pro Gln Phe Thr Pro Lys Val Ile Glu Ser Leu Ala Lys Asn
                260                 265                 270

Thr Lys Val Asn Val Gly Gln Leu Asp Pro Ile Gly Asp Lys Val Thr
                275                 280                 285

Leu Gly Lys Asn Ser Tyr Ala Thr Phe Leu Gln Ser Thr Ala Asp Ser
290                 295                 300

Tyr Met Glu Cys Leu Ala Lys
305                 310

<210> SEQ ID NO 10
<211> LENGTH: 1542
<212> TYPE: PRT
<213> ORGANISM: Haemophilus influenzae

<400> SEQUENCE: 10

Met Asn Lys Ile Tyr Arg Leu Lys Phe Ser Lys Arg Leu Asn Ala Leu
1               5                   10                  15

Val Ala Val Ser Glu Leu Thr Arg Gly Cys Asp His Ser Thr Glu Lys
                20                  25                  30

Gly Ser Glu Lys Pro Val Arg Thr Lys Val Arg His Leu Ala Leu Lys
            35                  40                  45

Pro Leu Ser Ala Ile Leu Leu Ser Leu Gly Met Ala Ser Ile Pro Gln
    50                  55                  60

Ser Val Leu Ala Ser Gly Leu Gln Gly Met Ser Val Val His Gly Thr
65                  70                  75                  80

Ala Thr Met Gln Val Asp Gly Asn Lys Thr Thr Ile Arg Asn Ser Val
                85                  90                  95

Asn Ala Ile Ile Asn Trp Lys Gln Phe Asn Ile Asp Gln Asn Glu Met
                100                 105                 110

Val Gln Phe Leu Gln Glu Asn Asn Ser Ala Val Phe Asn Arg Val
                115                 120                 125

Thr Ser Asp Gln Ile Ser Gln Leu Lys Gly Ile Leu Asp Ser Asn Gly
                130                 135                 140

Gln Val Phe Leu Ile Asn Pro Asn Gly Ile Thr Ile Gly Lys Glu Ala
145                 150                 155                 160

Ile Ile Asn Thr Asn Gly Phe Thr Ala Ser Thr Leu Asp Ile Ser Asn
                165                 170                 175
```

-continued

Glu Asn Ile Lys Ala Arg Asn Phe Thr Leu Glu Gln Thr Lys Asp Lys
            180                 185                 190

Ala Leu Ala Glu Ile Val Asn His Gly Leu Ile Thr Val Gly Lys Asp
        195                 200                 205

Gly Ser Val Asn Leu Ile Gly Gly Lys Val Lys Asn Glu Gly Val Ile
    210                 215                 220

Ser Val Asn Gly Gly Ser Ile Ser Leu Leu Ala Gly Gln Lys Ile Thr
225                 230                 235                 240

Ile Ser Asp Ile Ile Asn Pro Thr Ile Thr Tyr Ser Ile Ala Ala Pro
                245                 250                 255

Glu Asn Glu Ala Ile Asn Leu Gly Asp Ile Phe Ala Lys Gly Gly Asn
            260                 265                 270

Ile Asn Val Arg Ala Ala Thr Ile Arg Asn Lys Gly Lys Leu Ser Ala
        275                 280                 285

Asp Ser Val Ser Lys Asp Lys Ser Gly Asn Ile Ile Leu Ser Ala Lys
    290                 295                 300

Glu Gly Glu Ala Glu Ile Ser Gly Val Ile Ser Ala Gln Asn Gln Gln
305                 310                 315                 320

Ala Lys Gly Gly Lys Leu Met Ile Thr Gly Asp Lys Val Thr Leu Lys
                325                 330                 335

Thr Gly Ala Val Ile Asp Leu Ser Gly Lys Glu Gly Gly Glu Thr Tyr
            340                 345                 350

Leu Gly Gly Asp Glu Arg Gly Lys Gly Lys Asn Gly Ile Gln Leu Ala
        355                 360                 365

Lys Lys Thr Ser Leu Glu Lys Gly Ser Thr Ile Asn Val Ser Gly Lys
    370                 375                 380

Glu Lys Gly Gly Arg Ala Ile Val Trp Gly Asp Ile Ala Leu Ile Asp
385                 390                 395                 400

Gly Asn Ile Asn Ala Gln Gly Ser Asp Ile Ala Lys Thr Gly Gly Phe
                405                 410                 415

Val Glu Thr Ser Gly His Tyr Leu Ser Ile Asp Ser Asn Ala Ile Val
            420                 425                 430

Lys Thr Lys Glu Trp Leu Leu Asp Pro Asp Asn Val Thr Ile Glu Ala
        435                 440                 445

Pro Ser Leu Ser Arg Ala Asp Thr Asp Ile Ser Ser Glu Phe Pro Ile
    450                 455                 460

Gly Asp Gly Thr Glu Asn Ser Pro Lys Lys Asn Ala Asp Lys Thr Ile
465                 470                 475                 480

Leu Thr Asn Glu Thr Ile Ser Asn Phe Leu Gln Asn Ala Lys Val Met
                485                 490                 495

Asn Ile Thr Ala Lys Arg Lys Leu Thr Val Asn Ser Ser Ile Ser Ile
            500                 505                 510

Gly Ser Arg Ser His Leu Ile Leu His Ser Glu Gly Gln Gly Asp Gly
        515                 520                 525

Gly Val Gln Ile Asp Gly Asp Ile Thr Ser Glu Gly Gly Asn Leu Thr
    530                 535                 540

Ile Asn Ser Gly Gly Trp Val Asp Val His Lys Asn Ile Thr Leu Gly
545                 550                 555                 560

Thr Gly Phe Leu Asn Ile Thr Ala Gly Gly Ser Val Ala Phe Glu Lys
                565                 570                 575

Gly Gly Asn Asn Ala Arg Asn Ala Thr Asp Ala Gln Ile Thr Ala Gln
            580                 585                 590

Gly Thr Ile Thr Val Asn Lys Asp Asp Lys Gln Phe Arg Phe Asn Asn

```
                595                 600                 605
Val Ser Ile Asn Gly Thr Gly Glu Gly Leu Lys Phe Ile Ala Asn Gln
610                 615                 620

Asn Asn Phe Thr His Lys Phe Asp Gly Glu Ile Asn Ile Ser Gly Ile
625                 630                 635                 640

Val Thr Ile Asn Gln Thr Thr Lys Lys Asp Ala Lys Tyr Trp His Ala
                645                 650                 655

Ser Lys Asp Ser Tyr Trp Asn Val Ser Ser Leu Thr Leu Asn Asp Asp
                660                 665                 670

Ala Lys Phe Thr Phe Ile Lys Phe Val Asp Ser Gly Ser Asn Ser Gln
                675                 680                 685

Asp Leu Arg Ser Ala Arg Arg Phe Ala Gly Val His Phe Asn Gly
            690                 695                 700

Thr Gly Lys Thr Asn Phe Asn Ile Gly Ala Asn Ala Lys Ala Leu
705                 710                 715                 720

Phe Lys Leu Lys Pro Asn Ala Ala Thr Asp Pro Lys Lys Glu Leu Pro
                725                 730                 735

Ile Thr Phe Asn Ala Asn Ile Thr Ala Thr Gly Ser Ser Asp Ser Ser
                740                 745                 750

Val Met Phe Asp Ile His Ala Asn Leu Thr Ser Arg Ala Ala Ser Ile
                755                 760                 765

Asn Met Asp Ser Ile Asn Ile Thr Gly Gly Leu Asp Phe Ser Ile Thr
770                 775                 780

Ser His Asn Arg Asn Ser Asn Ala Phe Glu Ile Lys Lys Asp Leu Thr
785                 790                 795                 800

Ile Asn Ala Thr Asn Ser Lys Phe Ser Leu Lys Gln Thr Lys Asp Leu
                805                 810                 815

Phe Glu Asn Gln Tyr Thr Gly Asp Ala Ile Asn Ser Thr Arg Asn Leu
                820                 825                 830

Thr Ile Leu Gly Gly Asn Val Thr Leu Gly Gly Glu Asn Ser Ser Ser
                835                 840                 845

Asn Ile Thr Gly Asn Ile Thr Ile Ala Ala Glu Ala Asn Val Thr Leu
                850                 855                 860

Gln Ala Tyr Ala Asp Asn Ser Ile Lys Gly His Lys Lys Thr Leu
865                 870                 875                 880

Thr Leu Gly Asn Val Ser Thr Ser Gly Asn Leu Ser Leu Thr Gly Ser
                885                 890                 895

Lys Val Glu Val Lys Gly Asp Leu Ala Val Leu Asn Gly Ala Thr Phe
                900                 905                 910

Lys Gly Glu Thr Asn Asp Ser Leu Asn Ile Thr Gly Thr Phe Thr Asn
                915                 920                 925

Asn Gly Thr Ala Asp Ile Asn Ile Lys Arg Gly Val Val Asn Ile Gln
                930                 935                 940

Gly Asp Ile Thr Asn Lys Gly Leu Asn Ile Thr Thr Asn Ala Gln
945                 950                 955                 960

Lys Asn Gln Lys Thr Ile Ile Asn Gly Asn Ile Thr Asn Lys Lys Gly
                965                 970                 975

Asn Leu Asn Ile Thr Asn Asn Gly Asn Asp Thr Glu Ile Gln Ile Gly
                980                 985                 990

Gly Asn Ile Ser Gln Lys Glu Gly  Asn Leu Thr Ile Ser  Ser Asp Lys
                995                 1000                1005

Val Asn  Ile Thr Lys Gln Ile  Thr Ile Lys Ala Gly  Val Asp Glu
                1010                1015                1020
```

-continued

```
Lys Asp Ser Ser Ser Ser Thr Ala Ser Asp Ala Asn Leu Thr Ile
    1025                1030                1035

Lys Thr Lys Glu Leu Lys Leu Val Glu Asp Leu Asn Ile Ser Gly
    1040                1045                1050

Phe Asn Lys Ala Glu Ile Thr Ala Lys Asp Gly Ser Asp Leu Thr
    1055                1060                1065

Ile Gly Asn Thr Asn Ser Ala Asp Gly Thr Asn Ala Lys Lys Val
    1070                1075                1080

Thr Phe Asn Gln Val Lys Asp Ser Lys Ile Ser Ala Asn Asp His
    1085                1090                1095

Asn Val Thr Leu Asn Ser Lys Val Glu Thr Ser Gly Asn Thr Asp
    1100                1105                1110

Asn Thr Gly Asp Gly Ser Gly Asn Asn Ala Gly Leu Thr Ile Ala
    1115                1120                1125

Ala Lys Asn Val Glu Val Lys Asn Asn Ile Thr Ser Asn Lys Thr
    1130                1135                1140

Val Asn Ile Thr Ala Ser Glu Lys Leu Thr Thr Lys Ala Asp Ala
    1145                1150                1155

Thr Ile Asn Ala Thr Thr Gly Asn Val Glu Val Thr Ala Lys Thr
    1160                1165                1170

Gly Asp Ile Lys Gly Glu Val Lys Ser Thr Ser Gly Asn Val Asn
    1175                1180                1185

Ile Thr Ala Asn Gly Asp Thr Leu Asn Val Ser Asn Val Ser Gly
    1190                1195                1200

Asn Ala Val Thr Ile Thr Ala Asp Lys Gly Lys Leu Thr Thr Gln
    1205                1210                1215

Glu Ser Ser Thr Ile Ser Gly Thr Glu Ser Val Thr Thr Ser Ser
    1220                1225                1230

Gln Ser Gly Asp Ile Gly Gly Ala Ile Ser Gly Asn Thr Val Ser
    1235                1240                1245

Val Lys Ala Thr Asn Asp Leu Ile Thr Lys Ala Asn Ser Lys Ile
    1250                1255                1260

Glu Ala Lys Thr Gly Glu Ala Asn Val Thr Ser Ala Thr Gly Ile
    1265                1270                1275

Ile Gly Gly Thr Ile Ser Gly Asn Thr Val Asn Val Thr Ala Asn
    1280                1285                1290

Thr Gly Ser Leu Thr Ile Lys Gly Gly Ala Lys Val Asp Ala Thr
    1295                1300                1305

Asn Gly Ala Ala Thr Leu Thr Ala Glu Ser Gly Lys Leu Thr Thr
    1310                1315                1320

Gln Ala Gly Ser Thr Ile Thr Ser Asn Asn Gly Gln Thr Thr Leu
    1325                1330                1335

Thr Ala Lys Asp Gly Ser Ile Ala Gly Ser Ile Asp Ala Ala Asn
    1340                1345                1350

Val Thr Leu Asn Thr Thr Gly Thr Leu Thr Val Val Gly Ser
    1355                1360                1365

Ser Ile Asn Ala Asn Glu Gly Thr Leu Val Ile Asn Ala Gln Asp
    1370                1375                1380

Ala Thr Leu Asn Gly Asp Ala Ser Gly Asp Arg Thr Glu Val Asn
    1385                1390                1395

Ala Val Asn Ala Ser Gly Ser Gly Ser Val Thr Ala Val Thr Ser
    1400                1405                1410
```

-continued

Ser Ser Val Asn Ile Thr Gly Asp Leu Ser Thr Ile Asn Gly Leu
    1415                1420                1425

Asn Ile Ile Ser Lys Asn Gly Lys Asn Thr Val Val Leu Lys Gly
    1430                1435                1440

Ala Glu Ile Asp Val Lys Tyr Ile Gln Pro Gly Val Ala Ser Ala
    1445                1450                1455

Glu Glu Val Ile Glu Ala Lys Arg Ala Leu Glu Lys Val Lys Asp
    1460                1465                1470

Leu Ser Asp Glu Glu Arg Glu Thr Leu Ala Lys Leu Gly Val Ser
    1475                1480                1485

Ala Val Arg Phe Val Glu Pro Asn Asn Ala Ile Thr Val Asn Thr
    1490                1495                1500

Gln Asn Glu Phe Thr Thr Arg Pro Ser Ser Gln Val Thr Ile Ser
    1505                1510                1515

Glu Gly Lys Ala Cys Phe Ser Ser Gly Asp Gly Ala Ala Val Cys
    1520                1525                1530

Thr Asn Val Ala Asp Asp Gly Gln Gln
    1535                1540

<210> SEQ ID NO 11
<211> LENGTH: 1557
<212> TYPE: PRT
<213> ORGANISM: Haemophilus influenzae

<400> SEQUENCE: 11

Met Asn Lys Ile Tyr Arg Leu Lys Phe Ser Lys Arg Leu Asn Ala Leu
1               5                   10                  15

Val Ala Val Ser Glu Leu Thr Arg Gly Cys Asp His Ser Thr Glu Lys
            20                  25                  30

Gly Ser Glu Lys Pro Val Arg Thr Lys Val Arg His Leu Ala Leu Lys
        35                  40                  45

Pro Leu Ser Ala Ile Leu Leu Ser Leu Gly Met Ala Ser Ile Pro Gln
    50                  55                  60

Ser Val Leu Ala Ser Gly Leu Gln Gly Met Ser Val Val His Gly Thr
65                  70                  75                  80

Ala Thr Met Gln Val Asp Gly Asn Lys Thr Thr Ile Arg Asn Ser Val
                85                  90                  95

Asn Ala Ile Ile Asn Trp Lys Gln Phe Asn Ile Asp Gln Asn Glu Met
            100                 105                 110

Val Gln Phe Leu Gln Glu Ser Ser Asn Ser Ala Val Phe Asn Arg Val
        115                 120                 125

Thr Ser Asp Gln Ile Ser Gln Leu Lys Gly Ile Leu Asp Ser Asn Gly
    130                 135                 140

Gln Val Phe Leu Ile Asn Pro Asn Gly Ile Thr Ile Gly Lys Asp Ala
145                 150                 155                 160

Ile Ile Asn Thr Asn Gly Phe Thr Ala Ser Thr Leu Asp Ile Ser Asn
                165                 170                 175

Glu Asn Ile Lys Ala Arg Asn Phe Thr Leu Glu Gln Thr Lys Asp Lys
            180                 185                 190

Ala Leu Ala Glu Ile Val Asn His Gly Leu Ile Thr Val Gly Lys Asp
        195                 200                 205

Gly Ser Val Asn Leu Ile Gly Gly Lys Val Asn Glu Gly Val Ile
    210                 215                 220

Ser Val Asn Gly Gly Ser Ile Ser Leu Leu Ala Gly Gln Lys Ile Thr
225                 230                 235                 240

```
Ile Ser Asp Ile Ile Asn Pro Thr Ile Thr Tyr Ser Ile Ala Ala Pro
                245                 250                 255

Glu Asn Glu Ala Ile Asn Leu Gly Asp Ile Phe Ala Lys Gly Gly Asn
            260                 265                 270

Ile Asn Val Arg Ala Ala Asn Ile Arg Asn Gln Gly Lys Leu Ser Ala
        275                 280                 285

Asp Ser Val Ser Lys Asp Lys Ser Gly Asn Ile Val Leu Ser Ala Lys
    290                 295                 300

Glu Gly Glu Ala Glu Ile Gly Gly Val Ile Ser Ala Gln Asn Gln Gln
305                 310                 315                 320

Ala Lys Gly Gly Lys Leu Met Ile Thr Gly Asp Lys Val Thr Leu Lys
                325                 330                 335

Thr Gly Ala Val Ile Asp Leu Ser Gly Lys Glu Gly Gly Glu Thr Tyr
            340                 345                 350

Leu Gly Gly Asp Glu Arg Gly Glu Gly Lys Asn Gly Ile Gln Leu Ala
        355                 360                 365

Lys Lys Thr Ser Leu Glu Lys Gly Ser Thr Ile Asn Val Ser Gly Lys
    370                 375                 380

Glu Lys Gly Gly Arg Ala Ile Val Trp Gly Asp Ile Ala Leu Ile Asp
385                 390                 395                 400

Gly Asn Ile Asn Ala Gln Gly Lys Asp Ile Ala Lys Thr Gly Gly Phe
                405                 410                 415

Val Glu Thr Ser Gly His Tyr Leu Ser Ile Gly Asn Asp Ala Ala Val
            420                 425                 430

Glu Ala Lys Glu Trp Leu Leu Asp Pro Asp Asn Val Thr Ile Ser Asn
        435                 440                 445

Gly Asn Asp Asp Gln Ser Gln Leu Lys Asp Asp Arg Gly Asp Ser Pro
    450                 455                 460

Asn Lys Ile Leu Ala Asp Asn Lys His Thr Val Asn Asn Lys Thr Leu
465                 470                 475                 480

Ser Thr Ala Leu Ala Lys Gly Ile Gly Val Asn Ile Ser Ala Lys Lys
                485                 490                 495

Lys Val Asn Val Thr Ala Asp Ile Asn Val His Asn Gly Thr Leu Thr
            500                 505                 510

Leu His Ser Glu Gln Gly Gly Val Glu Ile Asn Gly Asp Ile Thr Ser
        515                 520                 525

Glu Gln Asn Gly Asn Leu Thr Ile Lys Ala Gly Ser Trp Val Asp Val
    530                 535                 540

His Lys Asn Ile Thr Ile Gly Thr Gly Phe Leu Asn Ile Thr Ala Gly
545                 550                 555                 560

Gly Ser Val Ala Phe Glu Lys Ala Gly Asp Lys Gly Arg Ala Ala
                565                 570                 575

Ser Asp Ala Lys Ile Val Ala Gln Gly Val Ile Thr Ala Gly Ser Gly
            580                 585                 590

Gln Asp Phe Arg Phe Asn Asn Val Ser Leu Asn Gly Thr Gly Arg Gly
        595                 600                 605

Leu Lys Phe Ile Thr Ala Lys Gly Asn Lys Gly Asn Phe Ser Ala Lys
    610                 615                 620

Phe Asp Gly Val Leu Asn Ile Ser Gly Asn Ile Ser Ile Asn His Thr
625                 630                 635                 640

Ala Asn Asn Gln Leu Ser Tyr Phe His Arg Gln Gly Tyr Thr Tyr Trp
                645                 650                 655
```

-continued

Asn Leu Thr Gln Leu Asn Val Asp Ser Asp Ser Ser Phe Ser Leu Thr
            660                 665                 670

Ser Ile Lys Asp Ala Ile Lys Val Gly Gly Tyr Asp Asn Ala Lys Asp
    675                 680                 685

Lys Lys Asn Thr Gly Gly Ile Gly Phe Thr Arg Asp Thr Ile Phe Asn
690                 695                 700

Val Lys Gln Gly Ala Arg Val Asp Ile Ser Tyr Thr Leu Pro Ile Ser
705                 710                 715                 720

Pro Val Lys Asn Ser Arg Ile Ala Ala Val Asn Phe Asp Gly Asn Ile
                725                 730                 735

Thr Val Lys Gly Gly Val Val Asn Leu Lys Phe Asn Ala Leu Ser
        740                 745                 750

Asn Asn Tyr Lys Thr Pro Gly Val Asn Ile Ser Ser Arg Phe Ile Asn
    755                 760                 765

Val Thr Glu Gly Ser Gln Leu Asn Ile Thr Gly Ser Met Pro Ser Thr
    770                 775                 780

Thr Leu Phe Asn Val Ala Asn Asp Leu Ile Ile Asn Ala Thr Asn Ser
785                 790                 795                 800

Phe Val Ser Ile Lys Glu Ile Glu Gly Thr Asp Thr His Leu Asp Thr
                805                 810                 815

Gly Leu Lys Val Asn Gly Asn Val Thr Ile Lys Gly Gly Asn Val Thr
        820                 825                 830

Leu Gly Ser Asn Lys Ala Lys Thr Lys Phe Asp Lys Asn Val Thr Val
        835                 840                 845

Glu Lys Gly Ala Asn Leu Thr Leu Ala Ser Ala Asn Phe Gly Asn His
850                 855                 860

Lys Gly Ala Leu Thr Val Ala Gly Asn Ile Asn Thr Gln Gly Lys Leu
865                 870                 875                 880

Val Ala Thr Gly Asp Thr Ile Asp Val Ser Gly Asp Phe Thr Val Gly
                885                 890                 895

Asn Asp Ala Thr Phe Asn Gly Asn Thr Asn Asn Leu Asn Ile Thr
                900                 905                 910

Gly Asn Phe Thr Asn Asn Gly Thr Ser Ile Ile Asp Val Lys Lys Gly
        915                 920                 925

Ala Ala Lys Leu Gly Asn Ile Thr Asn Glu Gly Ser Leu Asn Ile Thr
930                 935                 940

Thr His Ala Asn Thr Asn Gln Lys Thr Ile Ile Thr Gly Asn Ile Thr
945                 950                 955                 960

Asn Lys Lys Gly Asp Leu Asn Ile Arg Asp Asn Lys Asn Asn Ala Glu
                965                 970                 975

Ile Gln Ile Gly Gly Asn Ile Ser Gln Lys Glu Gly Asn Leu Thr Ile
            980                 985                 990

Ser Ser Asp Lys Val Asn Ile Thr Lys Gln Ile Thr Ile Lys Ala Gly
        995                 1000                1005

Val Asn Gly Glu Asn Ser Asp Ser Gly Thr Glu Asn Asn Ala Asn
    1010                1015                1020

Leu Thr Ile Lys Thr Lys Leu Glu Leu Thr Asn Asn Leu Asn
    1025                1030                1035

Ile Ser Gly Phe His Lys Ala Glu Ile Thr Ala Lys Asp Asn Ser
    1040                1045                1050

Asp Leu Ile Ile Gly Lys Ala Ser Ser Asp Ser Gly Asn Ala Gly
    1055                1060                1065

Ala Gln Lys Val Ile Phe Asp Lys Val Lys Asp Ser Lys Ile Ser

-continued

```
            1070                1075                1080

Ala Gly Asn His Asn Val Thr Leu Asn Ser Glu Val Glu Thr Ser
            1085                1090                1095

Asn Gly Asn Ser Asn Ala Ala Gly Asp Ser Asn Gly Asn Asn Ala
            1100                1105                1110

Gly Leu Thr Ile Ser Ala Lys Asp Val Ala Val Asn Asn Asn Ile
            1115                1120                1125

Thr Ser His Lys Thr Ile Asn Ile Ser Ala Thr Thr Gly Asn Val
            1130                1135                1140

Thr Thr Lys Glu Gly Thr Thr Ile Asn Ala Thr Thr Gly Gly Val
            1145                1150                1155

Glu Val Thr Ala Lys Thr Gly Asp Ile Lys Gly Gly Ile Glu Ser
            1160                1165                1170

Lys Ser Gly Gly Val Thr Leu Thr Ala Thr Gly Asp Thr Leu Ala
            1175                1180                1185

Val Gly Asn Ile Ser Gly Asn Thr Val Ser Val Thr Ala Asn Ser
            1190                1195                1200

Gly Thr Leu Thr Thr Lys Ala Asp Ser Thr Ile Lys Gly Thr Gly
            1205                1210                1215

Ser Val Thr Thr Leu Ser Gln Ser Gly Asp Ile Gly Gly Thr Ile
            1220                1225                1230

Ser Gly Lys Thr Val Ser Val Thr Ala Thr Thr Asp Ser Leu Thr
            1235                1240                1245

Val Lys Gly Gly Ala Lys Ile Asn Ala Thr Glu Gly Thr Ala Thr
            1250                1255                1260

Leu Thr Ala Ser Ser Gly Lys Leu Thr Thr Glu Ala Asn Ser Ala
            1265                1270                1275

Ile Ser Gly Ala Asn Gly Val Thr Ala Ser Ser Gln Ser Gly Asp
            1280                1285                1290

Ile Ser Gly Thr Ile Ser Gly Lys Thr Val Ser Val Thr Ala Thr
            1295                1300                1305

Thr Asp Ser Leu Thr Val Lys Gly Gly Ala Lys Ile Asn Ala Thr
            1310                1315                1320

Glu Gly Thr Ala Thr Leu Thr Ala Ser Ser Gly Lys Leu Thr Thr
            1325                1330                1335

Glu Ala Ser Ser Ser Ile Thr Ser Ala Lys Gly Gln Val Asp Leu
            1340                1345                1350

Ser Ala Arg Asp Gly Asn Ile Gly Gly Ser Ile Asn Ala Ala Asn
            1355                1360                1365

Val Thr Leu Asn Thr Thr Gly Thr Leu Thr Thr Val Lys Gly Ser
            1370                1375                1380

Ser Ile Asn Ala Asn Ser Gly Thr Leu Val Ile Asn Ala Glu Asp
            1385                1390                1395

Ala Lys Leu Asp Gly Thr Ala Ser Gly Asp Arg Thr Val Val Asn
            1400                1405                1410

Ala Thr Asn Ala Ser Gly Ser Gly Ser Val Thr Ala Val Thr Ser
            1415                1420                1425

Ser Ser Val Asn Ile Thr Gly Asp Leu Ser Thr Ile Asn Gly Leu
            1430                1435                1440

Asn Ile Ile Ser Lys Asn Gly Lys Asn Thr Val Val Leu Lys Gly
            1445                1450                1455

Ala Glu Ile Asp Val Lys Tyr Ile Gln Pro Gly Val Ala Ser Ala
            1460                1465                1470
```

```
Glu Glu Val Ile Glu Ala Lys Arg Ala Leu Lys Val Lys Asp
    1475                1480                1485

Leu Ser Asp Glu Glu Arg Glu Thr Leu Ala Lys Leu Gly Val Ser
    1490                1495                1500

Ala Val Arg Phe Val Glu Pro Asn Asn Ala Ile Thr Val Asn Thr
    1505                1510                1515

Gln Asn Glu Phe Thr Thr Arg Pro Ser Ser Gln Val Thr Ile Ser
    1520                1525                1530

Glu Gly Lys Ala Cys Phe Ser Ser Gly Asp Gly Ala Ala Val Cys
    1535                1540                1545

Thr Asn Val Ala Asp Asp Gly Gln Gln
    1550                1555

<210> SEQ ID NO 12
<211> LENGTH: 353
<212> TYPE: PRT
<213> ORGANISM: Haemophilus influenzae

<400> SEQUENCE: 12

Met Lys Lys Thr Ala Ile Ala Leu Val Val Ala Gly Leu Ala Ala
1               5                   10                  15

Ser Val Ala Gln Ala Ala Pro Gln Glu Asn Thr Phe Tyr Ala Gly Val
                20                  25                  30

Lys Ala Gly Gln Ala Ser Phe His Asp Gly Leu Arg Ala Leu Ala Arg
            35                  40                  45

Glu Lys Asn Val Gly Tyr His Arg Asn Ser Phe Thr Tyr Gly Val Phe
50                  55                  60

Gly Gly Tyr Gln Ile Leu Asn Gln Asn Asn Leu Gly Leu Ala Val Glu
65                  70                  75                  80

Leu Gly Tyr Asp Asp Phe Gly Arg Ala Lys Gly Arg Glu Lys Gly Lys
                85                  90                  95

Thr Val Ala Lys His Thr Asn His Gly Ala His Leu Ser Leu Lys Gly
                100                 105                 110

Ser Tyr Glu Val Leu Asp Gly Leu Asp Val Tyr Gly Lys Ala Gly Val
                115                 120                 125

Ala Leu Val Arg Ser Asp Tyr Lys Phe Tyr Glu Asp Ala Asn Gly Thr
            130                 135                 140

Arg Asp His Lys Lys Gly Arg His Thr Ala Arg Ala Ser Gly Leu Phe
145                 150                 155                 160

Ala Val Gly Ala Glu Tyr Ala Val Leu Pro Glu Leu Ala Val Arg Leu
                165                 170                 175

Glu Tyr Gln Trp Leu Thr Arg Val Gly Lys Tyr Arg Pro Gln Asp Lys
                180                 185                 190

Pro Asn Thr Ala Ile Asn Tyr Asn Pro Trp Ile Gly Ser Ile Asn Ala
            195                 200                 205

Gly Ile Ser Tyr Arg Phe Gly Gln Gly Ala Ala Pro Val Val Ala Ala
        210                 215                 220

Pro Glu Val Val Ser Lys Thr Phe Ser Leu Asn Ser Asp Val Thr Phe
225                 230                 235                 240

Ala Phe Gly Lys Ala Asn Leu Lys Pro Gln Ala Gln Ala Thr Leu Asp
                    245                 250                 255

Ser Ile Tyr Gly Glu Met Ser Gln Val Lys Ser Ala Lys Val Ala Val
                260                 265                 270

Ala Gly Tyr Thr Asp Arg Ile Gly Ser Asp Ala Phe Asn Val Lys Leu
```

```
            275                 280                 285
Ser Gln Glu Arg Ala Asp Ser Val Ala Asn Tyr Phe Val Ala Lys Gly
    290                 295                 300

Val Ala Ala Asp Ala Ile Ser Ala Thr Gly Tyr Gly Lys Ala Asn Pro
305                 310                 315                 320

Val Thr Gly Ala Thr Cys Asp Gln Val Lys Gly Arg Lys Ala Leu Ile
                325                 330                 335

Ala Cys Leu Ala Pro Asp Arg Arg Val Glu Ile Ala Val Asn Gly Thr
            340                 345                 350

Lys

<210> SEQ ID NO 13
<211> LENGTH: 460
<212> TYPE: PRT
<213> ORGANISM: Haemophilus influenzae

<400> SEQUENCE: 13

Met Lys Lys Phe Asn Gln Ser Leu Leu Ala Thr Ala Met Leu Leu Ala
1               5                   10                  15

Ala Gly Ser Ala Asn Ala Ala Phe Gln Leu Ala Glu Val Ser Thr
            20                  25                  30

Ser Gly Leu Gly Arg Ala Tyr Ala Gly Glu Ala Ala Ile Ala Asp Asn
        35                  40                  45

Ala Ser Val Val Ala Thr Asn Pro Ala Leu Met Ser Leu Phe Lys Thr
    50                  55                  60

Ala Gln Phe Ser Thr Gly Gly Val Tyr Val Asp Ser Arg Ile Asn Met
65                  70                  75                  80

Asn Gly Asp Val Thr Ser His Ala Thr Ile Val Thr Ser Ser Ser Gly
                85                  90                  95

Val Arg Ala Ile Lys Asp Gly Ser Ala Ser Ala Arg Asn Val Val Pro
            100                 105                 110

Gly Ala Phe Val Pro Asn Leu Tyr Phe Val Ala Pro Val Asn Asp Lys
        115                 120                 125

Phe Ala Leu Gly Ala Gly Met Asn Val Asn Phe Gly Leu Lys Ser Glu
    130                 135                 140

Tyr Asp Asp Ser Tyr Asp Ala Gly Ile Phe Gly Gly Lys Thr Asp Leu
145                 150                 155                 160

Ser Ala Ile Asn Leu Asn Leu Ser Gly Ala Tyr Arg Val Thr Glu Gly
                165                 170                 175

Leu Ser Leu Gly Leu Gly Val Asn Ala Val Tyr Ala Lys Ala Gln Val
            180                 185                 190

Glu Arg Asn Ala Gly Ile Leu Ala Glu Ser Val Asn Asp Asp Gln
        195                 200                 205

Val Lys Gly Ala Leu Leu Thr Leu Ser Glu Pro Phe Lys Asn Leu Asn
    210                 215                 220

Thr His Leu Pro Ser Lys Asp Lys Ser Val Val Ser Leu Gln Asp Arg
225                 230                 235                 240

Ala Ala Trp Gly Phe Gly Trp Asn Ala Gly Val Met Tyr Gln Phe Asn
                245                 250                 255

Glu Ala Asn Arg Ile Gly Leu Ala Tyr His Ser Lys Val Asp Ile Asp
            260                 265                 270

Phe Ala Asp Arg Thr Ala Thr Ser Leu Glu Ala Asn Val Ile Lys Ala
        275                 280                 285

Gly Lys Lys Ala Asp Leu Thr Phe Thr Leu Pro Asp Tyr Leu Glu Leu
```

-continued

```
            290                 295                 300
Ser Gly Phe His Gln Leu Thr Asp Lys Leu Ala Val His Tyr Ser Tyr
305                 310                 315                 320

Lys Tyr Thr His Trp Ser Arg Leu Thr Lys Leu His Ala Ser Phe Glu
                325                 330                 335

Asp Gly Lys Lys Ala Phe Asp Lys Glu Leu Gln Tyr Ser Asn Asn Ser
                340                 345                 350

Arg Val Ala Leu Gly Ala Ser Tyr Asn Leu Tyr Glu Lys Leu Thr Leu
            355                 360                 365

Arg Ala Gly Ile Ala Tyr Asp Gln Ala Ala Ser Arg His Gln Arg Ser
        370                 375                 380

Ala Ala Ile Pro Asp Thr Asp Arg Thr Trp Tyr Ser Leu Gly Ala Thr
385                 390                 395                 400

Tyr Lys Phe Thr Pro Asn Leu Ser Val Asp Leu Gly Tyr Ala Tyr Leu
                405                 410                 415

Lys Gly Lys Lys Val His Phe Lys Glu Val Lys Thr Ile Gly Glu Gln
                420                 425                 430

Arg Ser Leu Thr Phe Asp Thr Thr Ala Asn Tyr Thr Ser Gln Ala His
            435                 440                 445

Ala Asn Leu Tyr Gly Leu Asn Leu Asn Tyr Ser Phe
450                 455                 460
```